(12) United States Patent
Stelinski

(10) Patent No.: US 12,194,327 B2
(45) Date of Patent: Jan. 14, 2025

(54) **MATERIALS AND METHODS FOR MODIFYING *WOLBACHIA* AND PARATRANSFORMATION OF ARTHROPODS**

(71) Applicant: University of Florida Research Foundation, Inc., Gainesville, FL (US)

(72) Inventor: Kirsten Stelinski, Winter Haven, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 833 days.

(21) Appl. No.: 17/293,608

(22) PCT Filed: Nov. 13, 2019

(86) PCT No.: PCT/US2019/061094
§ 371 (c)(1),
(2) Date: May 13, 2021

(87) PCT Pub. No.: WO2020/102286
PCT Pub. Date: May 22, 2020

(65) Prior Publication Data
US 2022/0073866 A1   Mar. 10, 2022

Related U.S. Application Data

(60) Provisional application No. 62/767,176, filed on Nov. 14, 2018.

(51) Int. Cl.
*A62C 3/02* (2006.01)
*C12N 1/20* (2006.01)
*C12N 9/22* (2006.01)
*C12N 15/11* (2006.01)
*C12N 15/74* (2006.01)
*C12N 15/86* (2006.01)

(52) U.S. Cl.
CPC .......... *A62C 3/0214* (2013.01); *A62C 3/0257* (2013.01); *C12N 1/205* (2021.05); *C12N 9/22* (2013.01); *C12N 15/111* (2013.01); *C12N 15/74* (2013.01); *C12N 15/86* (2013.01); *C12N 2310/20* (2017.05)

(58) Field of Classification Search
CPC ..... C12N 15/74; C12N 15/86; C12N 2310/20
See application file for complete search history.

(56) References Cited

U.S. PATENT DOCUMENTS

| | | |
|---|---|---|
| 3,715,843 A | 2/1973 | Ballinger |
| 4,858,395 A | 8/1989 | McQuirk |
| 4,994,317 A | 2/1991 | Dugan et al. |
| 5,047,449 A | 9/1991 | Pastureau |
| 5,423,150 A | 6/1995 | Hitchcock |
| 5,608,992 A | 3/1997 | Floyd |
| 5,860,251 A | 1/1999 | Gleich |
| 5,931,233 A | 8/1999 | La et al. |
| 5,968,669 A | 10/1999 | Liu et al. |
| 6,810,626 B2 | 11/2004 | Meyer et al. |
| 7,395,869 B2 | 7/2008 | Schnabel et al. |
| 7,868,222 B1 * | 1/2011 | Dobson .............. A01K 67/0339 800/13 |
| 8,006,447 B2 | 8/2011 | Beele |
| 8,127,387 B2 | 3/2012 | Tygh |
| 9,381,387 B2 | 7/2016 | Douglas |
| 9,956,445 B2 | 5/2018 | Enk, Sr. |
| 11,268,100 B2 * | 3/2022 | Bordenstein ........... C12N 15/74 |
| 2005/0022466 A1 | 2/2005 | Kish et al. |
| 2005/0170725 A1 | 8/2005 | Kimener |
| 2009/0301001 A1 | 12/2009 | Kish et al. |
| 2010/0269449 A1 | 10/2010 | Bush et al. |
| 2012/0227990 A1 | 9/2012 | Burnham |
| 2013/0048317 A1 | 2/2013 | Charlton |
| 2013/0118764 A1 | 5/2013 | Porter |
| 2015/0083443 A1 | 3/2015 | Thompson |
| 2016/0047120 A1 | 2/2016 | Davis et al. |
| 2016/0345556 A1 * | 12/2016 | Hay .................. A01K 67/0339 |
| 2020/0316421 A1 | 10/2020 | Patzelt |

FOREIGN PATENT DOCUMENTS

| | | |
|---|---|---|
| WO | 2013/176772 A1 | 11/2013 |
| WO | 2017/181043 A1 | 10/2017 |
| WO | WO-2017214476 A1 * | 12/2017 ......... A01K 67/0337 |

OTHER PUBLICATIONS

Kent BN, Bordenstein SR. Phage WO of Wolbachia: lambda of the endosymbiont world. Trends Microbiol. Apr. 2010;18(4):173-81. doi: 10.1016/j.tim.2009.12.011. Epub Jan. 18, 2010. PMID: 20083406; PMCID: PMC2862486. (Year: 2010).*
Biochemistry. Feb. 21, 2017; 56(7): 907-918. doi: 10.1021/acs.biochem.6b00870. (Year: 2017).*
Ausubel et al., Short Protocols in Molecular Biology, 3rd ed., Wiley & Sons (1995).
Badawi et al., Signs of neutralization in a redundant gene involved in homologous recombination in Wolbachia endosymbionts, Genome Biol. Evol., 6(10):2654-2664 (2014).
Baum et al., *Drosophila* cell lines as model systems and as an experimental tool, Methods in Molecular Biology, 420:391-424 (2008).
Buster et al., Preparation of *Drosophila* S2 cells for light microscopy, J. Vis. Exp., 40:e1982 (2010).
Chu et al., Inter-Population Variability of Endosymbiont Densities in the Asian Citrus Psyllid (*Diaphorina citri* Kuwayama), Microb. Ecol., 71(4):999-1007 (2016).
Dobson et al., A novel technique for removing Wolbachia infections from *Aedes albopictus* (Diptera: Culicidae), J. Med. Entomol., 38(6):844-849 (2001).

(Continued)

*Primary Examiner* — Christopher M Babic
*Assistant Examiner* — Joel D Levin
(74) *Attorney, Agent, or Firm* — MARSHALL, GERSTEIN & BORUN LLP

(57) ABSTRACT

The present disclosure is directed to materials and method for genetically modifying *Wolbachia*, as well as arthropods comprising the modified *Wolbachia*.

10 Claims, 12 Drawing Sheets

Specification includes a Sequence Listing.

(56) References Cited

OTHER PUBLICATIONS

Dossi et al., Population dynamics and growth rates of endosymbionts during *Diaphorina citri* (Hemiptera, Liviidae) ontogeny, Microb. Ecol., 68(4):881-9 (2014).

Eleftherianos et al., Endosymbiotic bacteria in insects: guardians of the immune system?, Front Physiol., 4:1-10 (2013).

Fonfara et al., Phylogeny of Cas9 determines functional exchangeability of dual-RNA and Cas9 among orthologous type II CRISPR-Cas systems, Nucleic Acids Research, 42(4):2577-2590 (2014).

Gamston et al., Maintaining Wolbachia in cell-free medium, J. Vis. Exp., 5:e223 (2007).

Goeddel, Gene Expression Technology: Methods in Enzymology 185, Academic Press, San Diego, CA (1990).

Hancock et al., Strategies for introducing Wolbachia to reduce transmission of mosquito-borne diseases, PLoS Negl. Trop. Dis., 5(4):e1024 (2011).

Hughes et al., Wolbachia infections are virulent and inhibit the human malaria parasite Plasmodium falciparum in Anopheles gambiae, PLoS Pathog., 7(5):1002043 (2011).

International Application No. PCT/US19/61094, International Preliminary Report on Patentability, mailed May 27, 2021.

International Application No. PCT/US19/061094, International Search Report and Written Opinion, mailed Feb. 7, 2020.

Jiang et al., Multigene editing in the *Escherichia coli* genome via the CRISPR-Cas9 system, App. Environ. Microbiol., 81(7):2506-2515 (2015).

Jiang et al., RNA-guided editing of bacterial genomes using CRISPR-Cas systems, Nat. Biotechnol., 31(3):233-239 (2013).

Jinek et al., A programmable dual-RNA-guided DNA endonuclease in adaptive bacterial immunity, Science, 337(6096):816-821 (2012).

Kambris et al., Immune activation by life-shortening Wolbachia and reduced filarial competence in mosquitoes, Science, 326:1374-136 (2009).

Kent et al., Phage WO of Wolbachia: lambda of the endosymbiont world, Trends in Microbiology, 18(4):173-181 (2010).

Ma et al., Pol III Promoters to Express Small RNAs: Delineation of Transcription Initiation, Molecular Therapy—Nucleic Acids, 3(5):e161 (2014).

Moreira et al., A Wolbachia symbiont in Aedes aegypti limits infection with dengue, Chikungunya, and Plasmodium, Cell., 139(7):1268-1278 (2009).

O'Neill et al., In vitro cultivation of Wolbachia pipientis in an Aedes albopictus cell line, Insect Mol. Biol., 6(1):33-39 (1997).

Rachek et al., Transformation of Rickettsia prowazekii to rifampin resistance, J. Bacteriol., 180(8):2118-2124 (1998).

Ragson et al., Survival of Wolbachia pipientis in cell-free medium, Appl. Environ. Microbiol., 72(11):6934-6937 (2006).

Salles et al., Use of endophytic diazotrophic bacteria as a vector to express the cry3A gene from Bacillus thuringiensis, Brazilian Journal of Microbiology, 31(3):154-160 (2000).

Sambrook et al., Molecular cloning: A laboratory manual, Cold Spring Harbor (New York): Cold Spring Harbor Laboratory Press, 1, 680p (2001).

Stevens et al., Male-Killing, Nematode Infections, Bacteriophage Infection, and Virulence of Cytoplasmic Bacteria in the Genus Wolbachia, Annual Review of Ecology and Systematics, 32:519-545 (2001).

Stouthamer et al., Wolbachia pipientis: microbial manipulator of arthropod reproduction, Annu. Rev. Entomol., 53:71-102 (1999).

Texeira et al., The bacterial symbiont Wolbachia induces resistance to RNA viral infections in *Drosophila melanogaster*, PLos Biol., 6(12):e2 (2008).

Thiem, A Genetic Manipulation System For Wolbachia In Mosquitoes. Grant proposal [online], USDA Research, Education, & Economics Information System, Sep. 30, 2017.

U.S. Appl. No. 16/679,232, Requirement for Restriction/Election, mailed Mar. 9, 2021.

Untergrasser et al., Primer3—new capabilities and interfaces, Nucleic Acids Res., 40(15):e115 (2012).

Werren et al., Wolbachia: master manipulators of invertebrate biology, Nat. Rev. Microbiol., 6(10):741-751 (2008).

Werren, Biology of Wolbachia, Annu. Rev. Entomol., 42:587-609 (1997).

Yen et al., The etiological agent of cytoplasmic incompatibility in Culex pipiens, J. Invertebr. Pathol., 22(2):242-250 (1973).

Zug et al., Still a host of hosts for Wolbachia: analysis of recent data suggests that 40% of terrestrial arthropod species are infected, PLos One, 7(6):e38544 (2012).

* cited by examiner

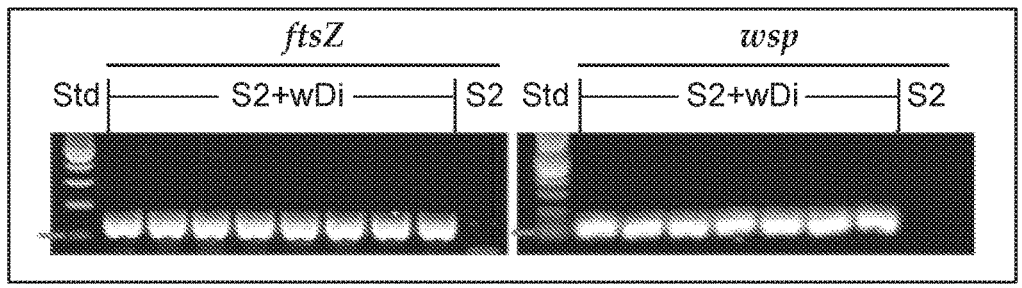

Figure 1. Verification of wDi in cell culture. The PCR amplification products of the established *in vitro* wDi infected S2 cells (S2+wDi) and an uninfected (S2) cell lines using the general-*Wolbachia* (*ftsZ*) and the specific-wDi (*wsp*) primer sets. A molecular size standard (Std) is shown (100 base pair (bp) DNA Ladder; NEB). The red markers indicate the 100 bp.

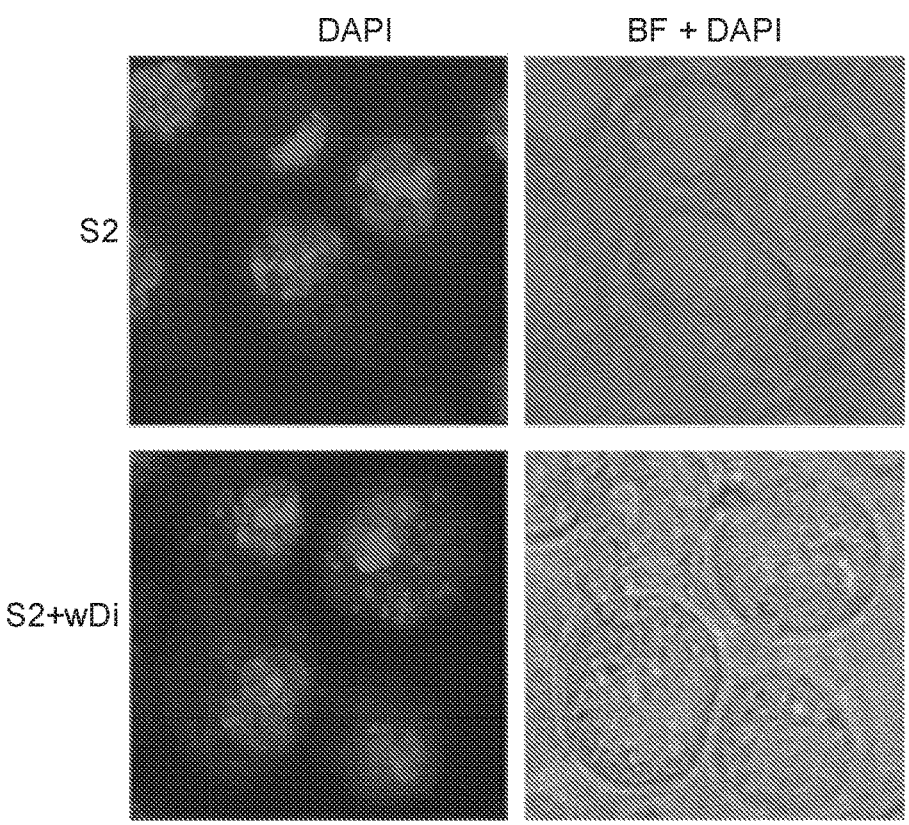

Figure 2. Intracellular location of wDi in S2 cells. Confocal images of fixed S2 and S2+wDi cells, acquired using DAPI (blue) filter and bright field (bf). DAPI stained the S2 cells nuclei in addition to wDi chromosomes.

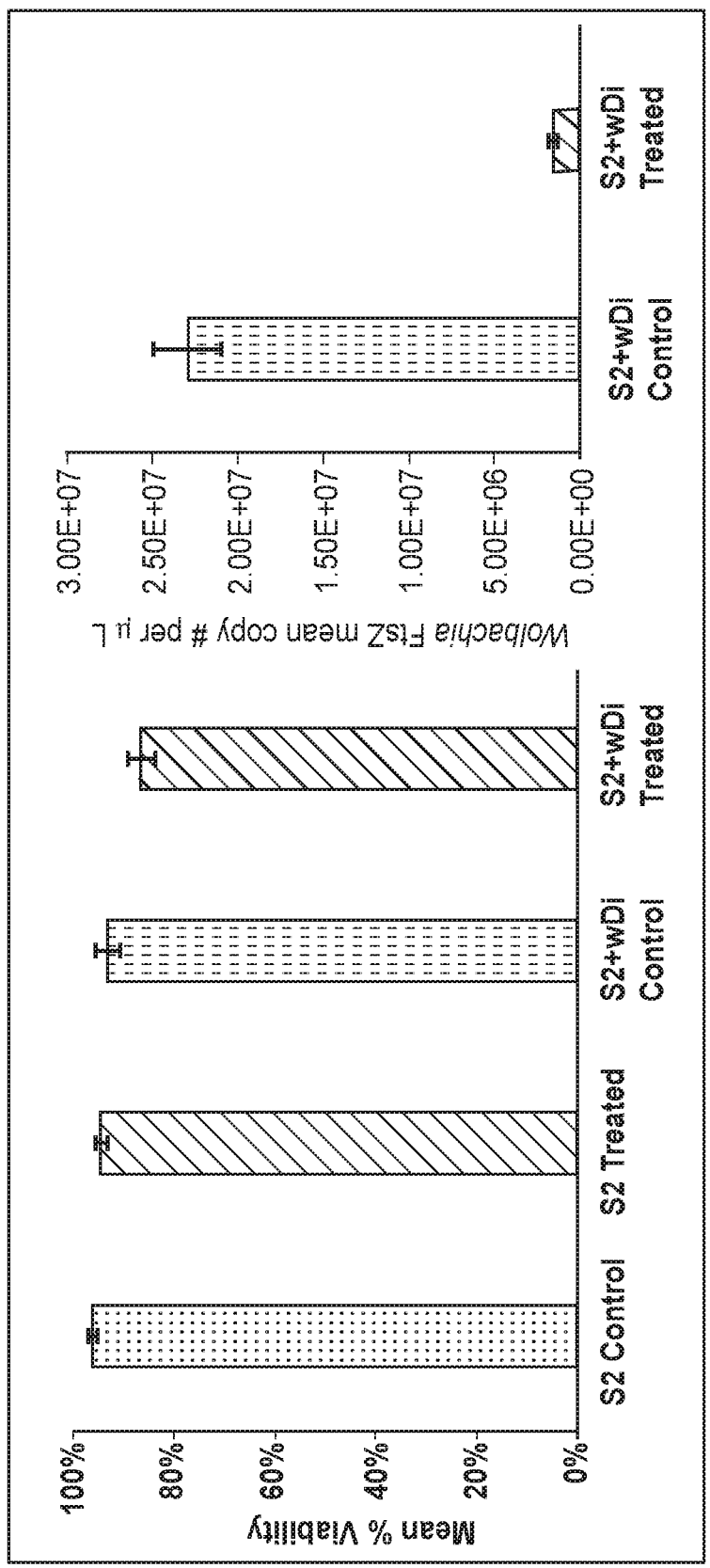

Figure 3. Reduction of wDi infection in S2 cells with tetracycline treatment. Infected and uninfected S2 cells with wDi were untreated (control) and treated with tetracycline for three days in S2 medium (A & B). Treatment with tetracycline had no significant effect on S2 cells survival (A). *Wolbachia* FtsZ mean copy number was determined for control and treated samples. (B) shows that wDi infection in S2 cells was reduced by three day of tetracycline treatment.

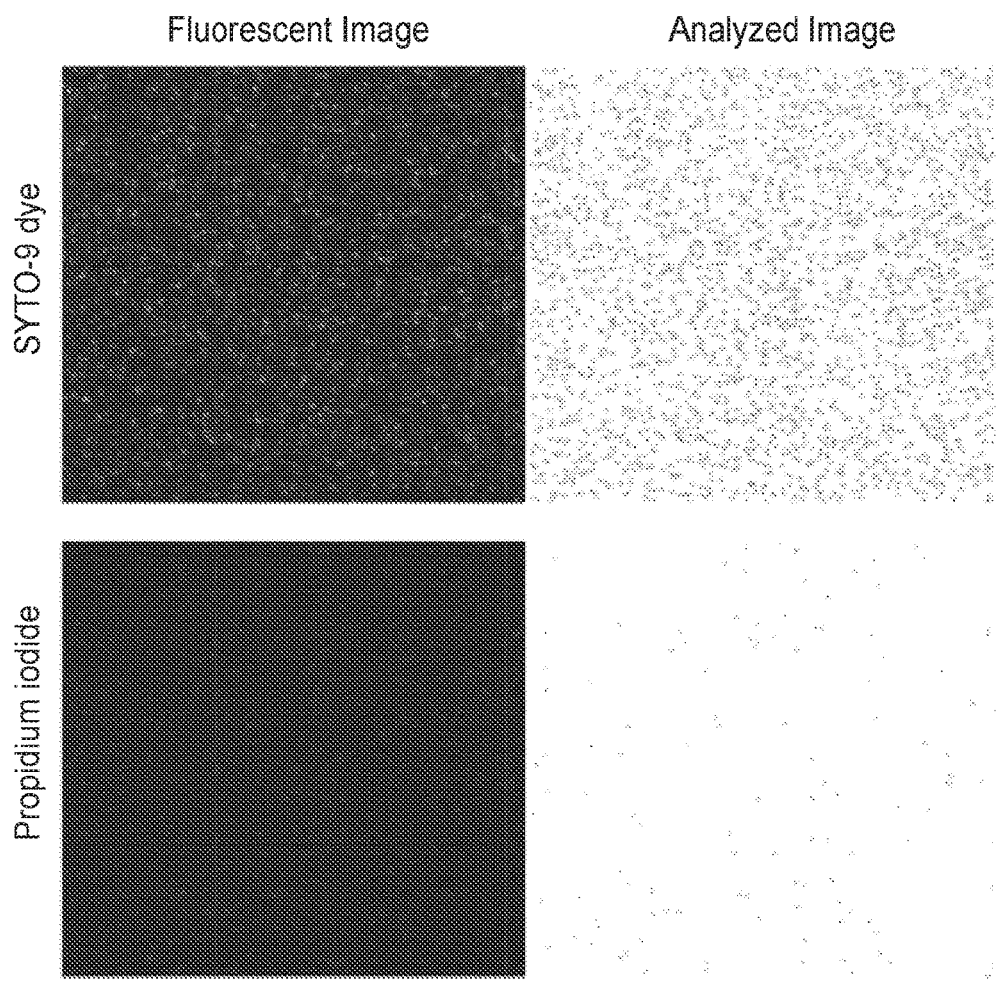

Figure 4. Purified wDi cells remain viable. wDi cells were extracted and purified from S2 cells, and were visualized with the BacLight live-dead stain. wDi cells were stained with green SYTO-9 dye (top row), and dead wDi cells are stained red with Propidium iodine (bottom row) (fluorescent images). For both fluorescent images, the cells were outlined and counted (second column) using ImageJ program (analyzed images). There were 2980 total cells, 2853 live cells and 127 dead cells; percent viability of 95.7% and percent mortality of 4.3%. For all subsequent wDi cell extractions and purifications the percent viabilities were >95% (data not shown).

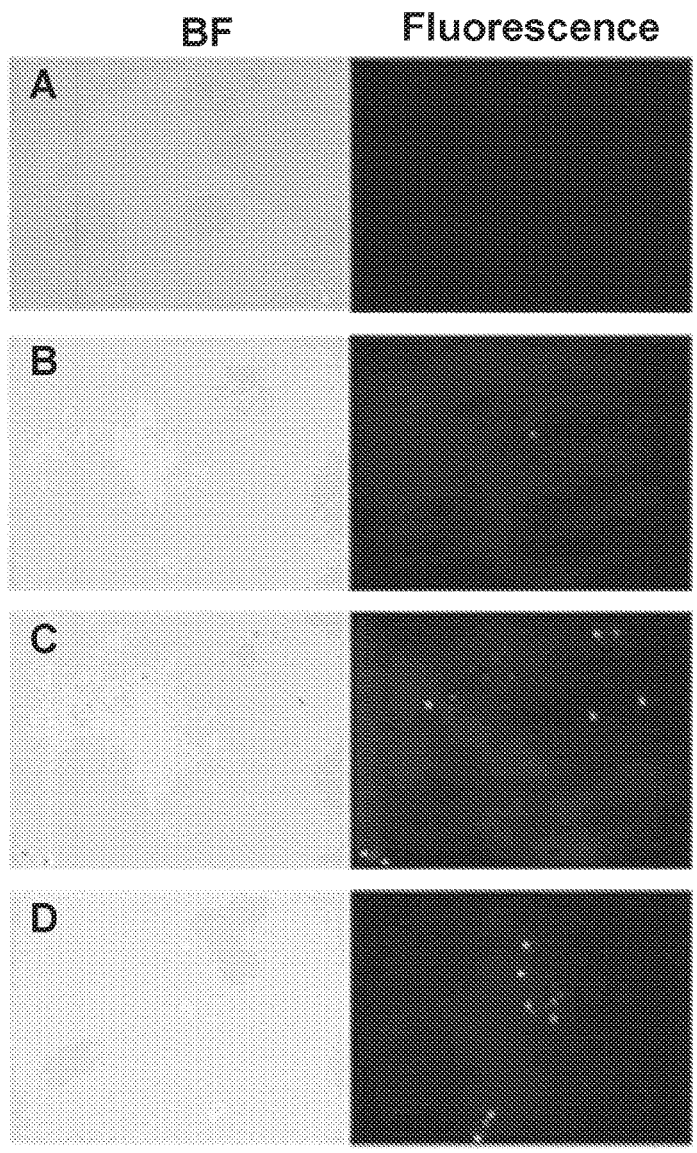

Figure 5. Electroporation of fluorescein-labeled dsRNA on purified wDi. Purified wDi cells were electroporated with fluorescein-labeled dsRNA (dsRNA^FL). All cells were mixed in with 30mM dsRNA^FL and were imaged at 48 hours-post-electroporation. The control cells that were not electroporated (A), and cells that were electroporated with the highest number of pulses (25x) (B) had no to little dsRNA^FL signal. Samples that were electroporated with 18 (C) and 10 (D) pulses had multiple wDi cells with dsRNA^FL signal.

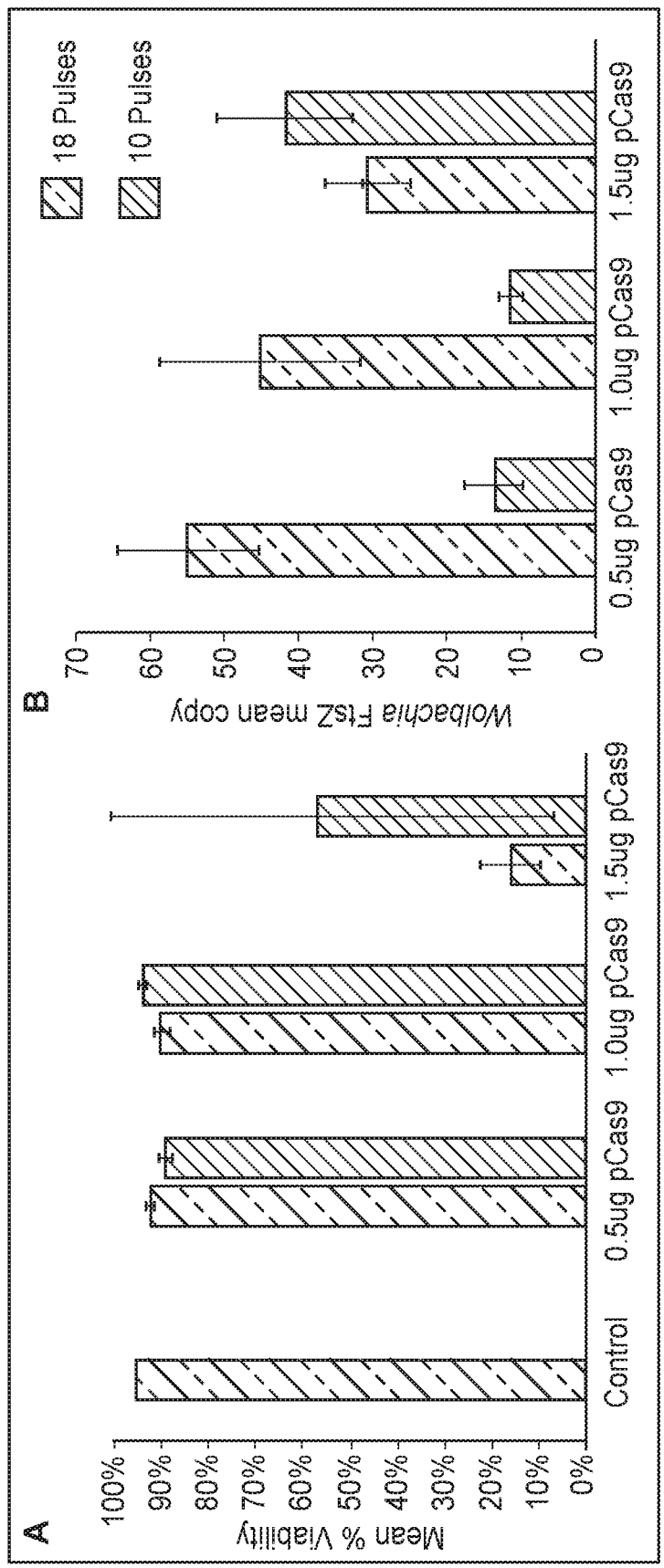

Figure 6. Viability of S2+wDi cells after electroporation with pCas9. Cells were counted after two days of reinfection of wDi (A & B). There were two biological replicated for each sample. Control samples were electroporated with no DNA at 18 pulses (A). Electroporation with 1.5ug of pCas9 had significant effect on viability of S2+wDi (A). *Wolbachia* FtsZ mean copy number was determined for each concentration of pCas9 electroporated (B).

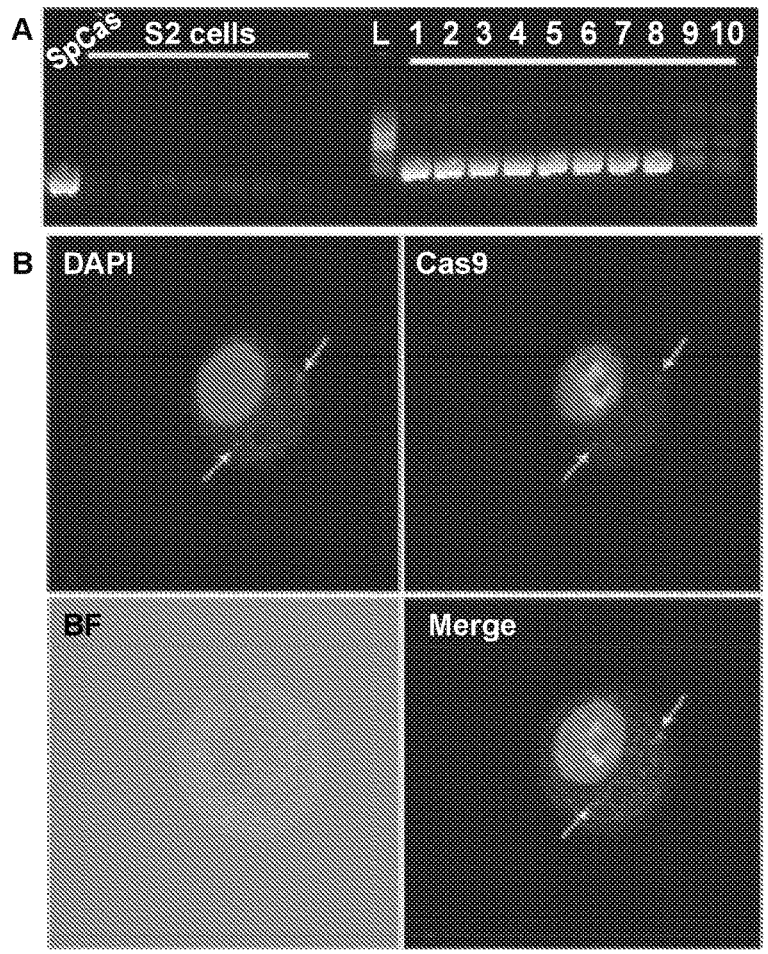

Figure 7. Detection of DNA and protein from pCas9 in S2+wDi$^{pCas9}$ cells. (A) are the PCR amplification produces of pCas9 (primers design to amplify a *chloramphenicol resistant* gene fragment found in the plasmid DNA), (L) 100 bp ladder; DNA of samples are from two day post re-infection; #1-8 are samples that were electroporated with pCas9; sample #9 is the electroporation control with no DNA; and sample #10 is the no DNA and no electroporation control. Confocal images of S2+wDi$^{pCas9}$ cells labeled with Cas9 and DAPI (B). White arrows indicate cytoplasmic wDi that express Cas9.

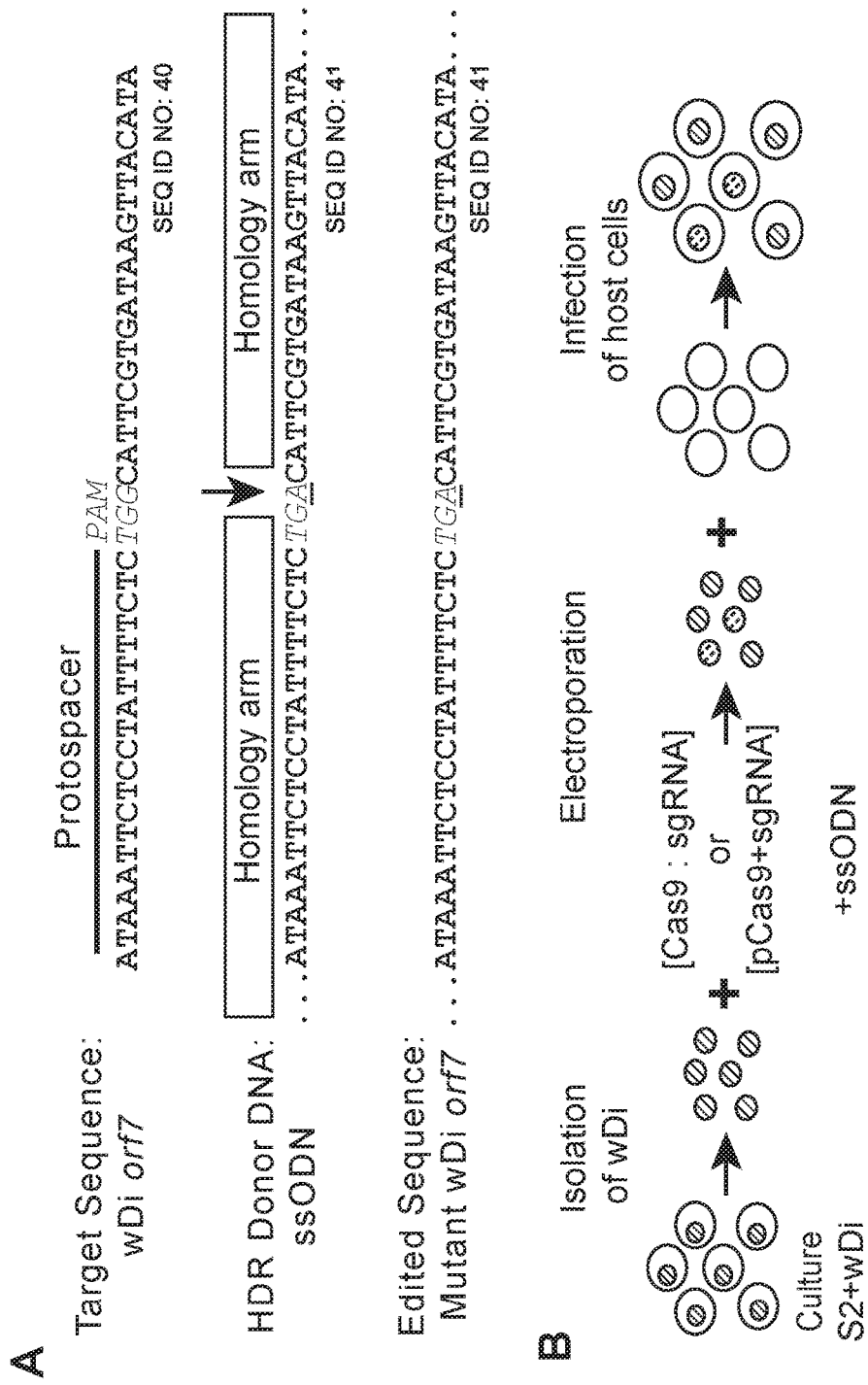

Figure 8. Strategy of single nucleotide mutation in wDi using homology-directed repair (HDR) with CRISPR/Cas9 system. (A) Nucleotide sequences of wild-type wDi *orf7* targeted region, the HRD donor DNA (ssODN) and the resulting mutated wDi *orf7*. The nucleotide targeted for exchange is highlighted in blue. (B) Schematic diagram outlining the steps used to transform wDi with either the protein or plasmid base systems in combination with ssODN. Grey circles represent S2 cells, yellow circles represent wDi, and red circles represent transformed wDi cells.

Figure 9. **Confirmed point mutation in wDi *orf7*.** wDi cells were transfected with CRISPR/Cas9 components followed by a 48 hours incubation period. DNA was isolated, the targeted region was amplified and subjected to Sanger sequencing. (A) Depicts experiments conducted with the plasmid base system. (B-C) Depicts experiments conducted with the protein base system; and in (C), 1-3 are technical replicates.

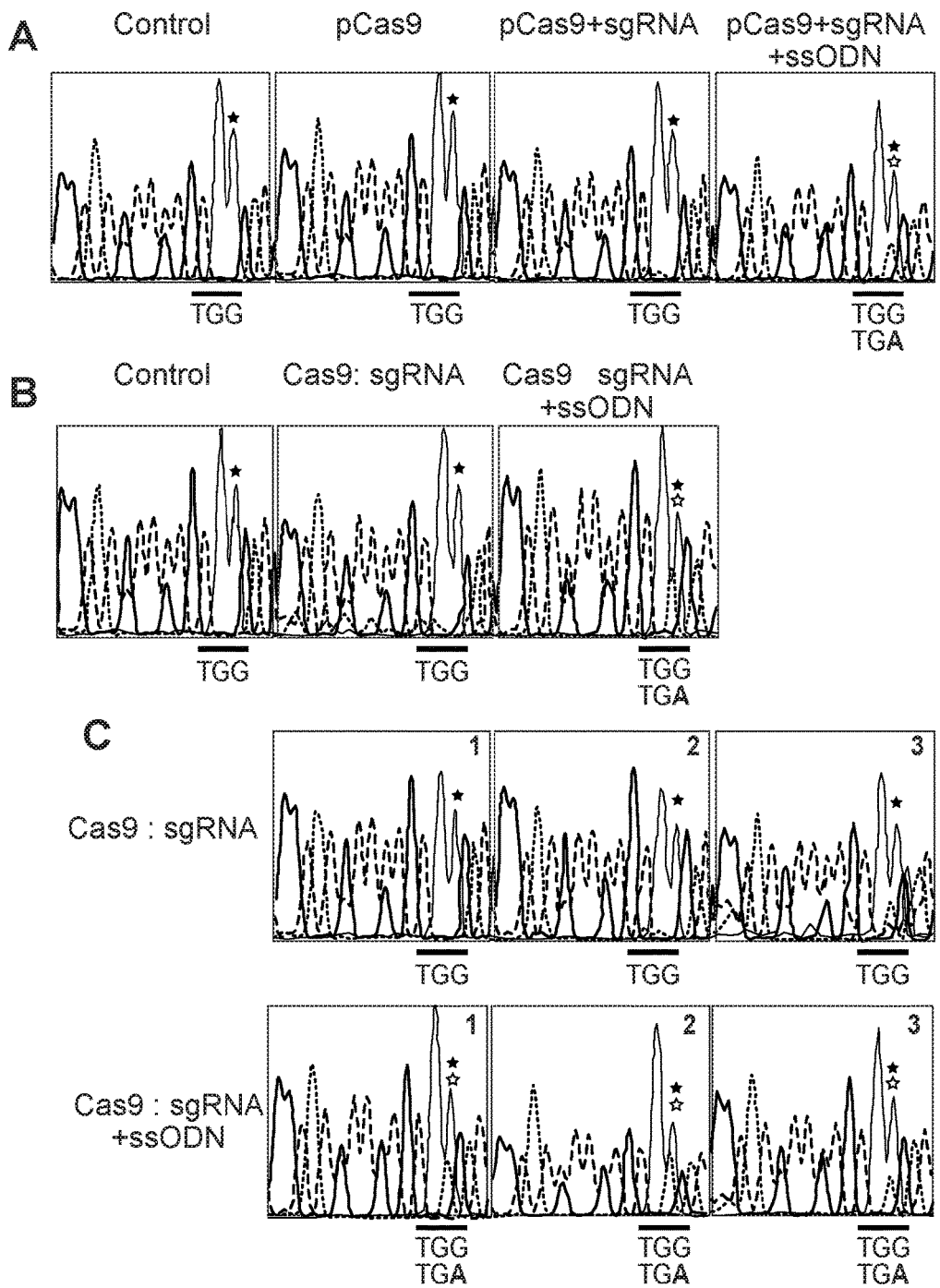

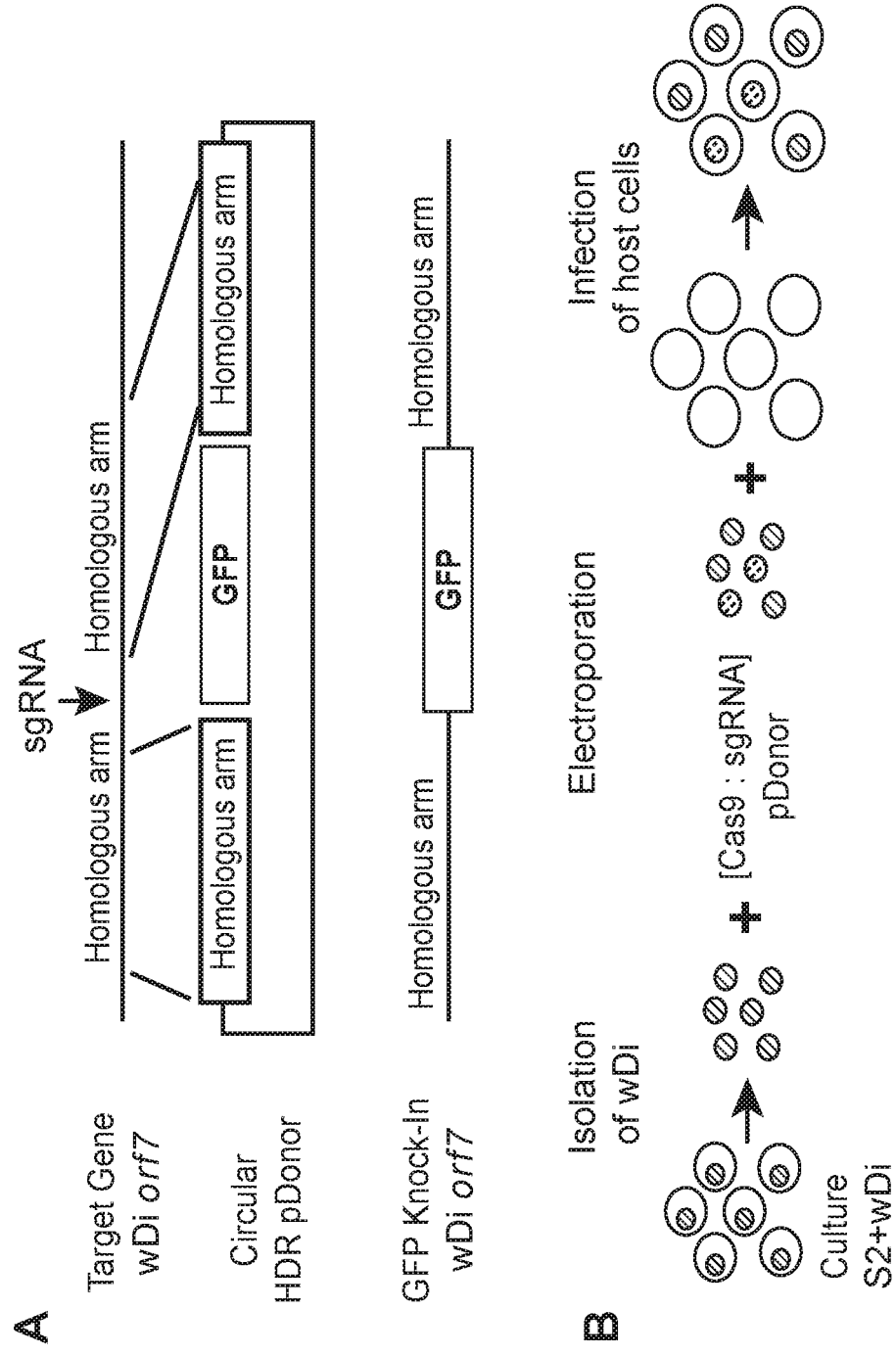

Figure 10. Approach for gene insertion using homology-directed repair with CRISPR/Cas9 system in wDi. (A) Nucleotide sequences of wild-type wDi *orf7* targeted region, the homology-directed repair (HRD) plasmid donor DNA (pDonor) and the resulting incorporation of the transgene in wDi. (B) Schematic diagram outlining the steps used to transform wDi with the protein base systems. Grey circles represent S2 cells, yellow circles represent wDi, and green circles represent transformed wDi cells.

Figure 11. Knock-in of GFP in wDi by HDR with CRISPR/Cas9 technology. (A & B) PCR-based genotyping using primer to confirmed integration of GFP in wDi cells. Electroporated with no pDonor wDi cells were used as negative controls (CONT). (C) Using FACS, transformed wDi cells were enriched on the basis of GFP intensity (x-axis) after 2d of electroporation. wDi$^{+dsRNAFlu}$ cells were used as positive controls. Y-axis is the side scatter area (SSC-A). Samples with in the grey area account for GFP+ cells. (D) Wide-field fluorescence microscopy images of live sorted wDi$^{+GFP}$ cells. (E) Confocal miscopy of live S2+wDi$^{+GFP-R}$ cells; samples were stained with Hoechst 33342 (blue).

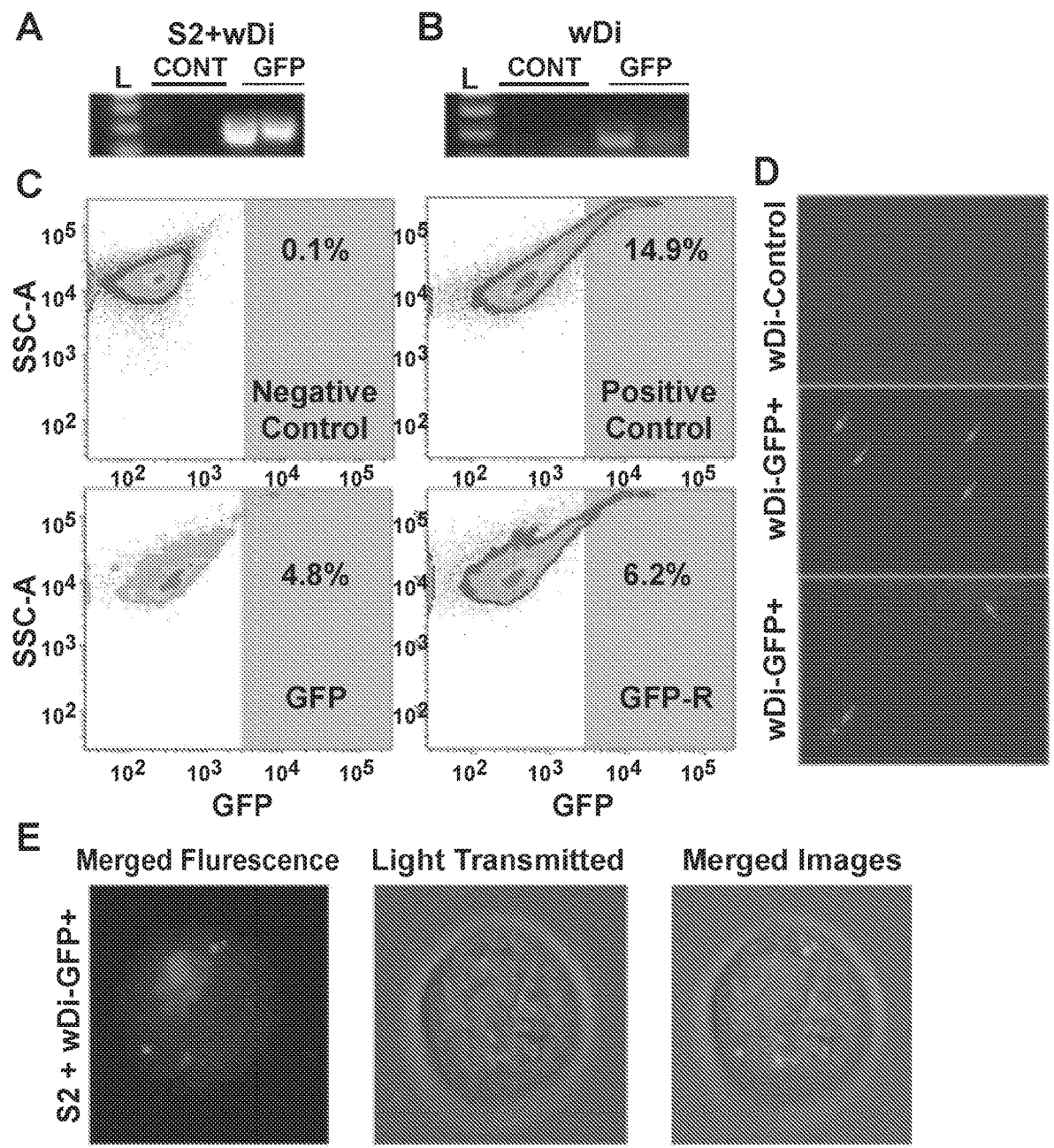

Figure 12. Insertion of *toxin* genes in wDi by HDR with CRISPR/Cas9 system. (A) Strategy for *toxin* gene insertion. Electroporation of wDi were conducted with different pDonors; pCry3Aa, pCry3Aa-R, pCyt2Ca1, pCyt2Ca1-R, pGNA3, pGNA3-R. (B-G) DNA from transformed and non-transformed negative control (NC) cells were used for PCR analysis. Two biological replicates of each sample are shown. Different PCR primers used in the study: Cry3Aa-f, Cry3Aa-r for *Cry3Aa* (B), Cry3Aa-R-f, Cry3Aa-R-r for *Cry3Aa-R* (C), Cyt2Ca1-f, Cyt2Ca1-r for *Cyt2Ca1* (D), Cyt2Ca1-R-f, Cyt2Ca1-R-r for *Cyt2Ca1-R* (E), GNA3-f, GNA3-r for *GNA3* (F), and GNA3-R-f, GNA3-R-r for *GNA3-R* (G).

Figure 13. Vertical transmission of transformed wDi⁺ in *D. citri*. (A) *In vivo* visualization of *D. citri* nymphs. Nymph one was injected in the abdominal segment and nymph two was injected twice in the mesothorax with stained Hoechst 33342 (nuclei) wDi$^{+GFP-R}$. Yellow arrows indicate injection locations. Red arrows indicate exogenous transformed cells that are positive for both nuclei stain and GFP signal. (B & C) Parental *D. citri* were injected with wDi$^{+Cry3Aa-R}$, their offspring F1 (B) & F3 (C) were individually processed for PCR analysis. (B) Detection of wDi$^{+Cry3Aa-R}$ in *D. citri* adults are labeled with green positive symbol and (C) non-wDi$^{+Cry3Aa-R}$ samples were labeled with red

MATERIALS AND METHODS FOR MODIFYING *WOLBACHIA* AND PARATRANSFORMATION OF ARTHROPODS

CROSS-REFERENCE TO RELATED APPLICATION

The present application claims the benefit of priority to U.S. Provisional Application No. 62/767,176 filed Nov. 14, 2018, the disclosure of which is incorporated herein by reference in its entirety.

STATEMENT ON U.S. GOVERNMENT INTEREST

This invention was made with government support under D16AP00031 awarded by The United States Department of Defense. The government has certain rights in the invention

FIELD OF THE INVENTION

The present disclosure is directed to materials and method for genetically modifying *Wolbachia*, as well as the arthropods comprising the modified *Wolbachia*.

BACKGROUND

The genus *Wolbachia* are Alpha-proteobacteria that are obligated cytoplasmic endosymbionts of eukaryotic cells (Werren, 1997). These maternally transmitted bacteria, which are widespread among numerous arthropod and nematode species (Stevens et al., 2001; Zug and Hammerstain, 2012), can alter host reproduction by causing parthenogenesis, feminization, embryonic male killing and cytoplasmic incompatibility (Stouthamer et al., 1999; Werren et al., 2008), reproductive manipulations that increase the fitness of infected females and benefits the spread of the bacterium within a host population. Cytoplasmic incompatibility is the most common reproductive phenotype, occurring when sperm from *Wolbachia*-infected males is incompatible with eggs from uninfected females or females that do not harbor the same *Wolbachia* strain, resulting in embryonic death (Yen and Barr, 1971). In addition, *Wolbachia* strains can provide its hosts with protection against different types of infective agents (Teixeira et al., 2008; Moreira et al., 2009; Kambris et al., 2009; Eleftherianos et al., 2013) and potentially interfere the transmission of insect-borne pathogens or parasites (Hancock et al., 2011; Hughes et al., 2011).

*Wolbachia*'s capacity to alter host reproduction and fitness demonstrates the potential of these bacteria as an instrument for the management of insect vectors.

SUMMARY

In one aspect, described herein is a method comprising (a) transforming *Wolbachia* bacterium with an exogenous nucleic acid using a CRISPR-Cas9 nuclease to insert the nucleic acid into the genome of the bacterium, thereby producing a genetically transformed bacterium; and (b) introducing the genetically transformed bacterium into an arthropod.

In some embodiments, the method includes isolating the bacterium from an arthropod host before the transforming step. In this instance, the arthropod host may be the same type of arthropod into which the genetically transformed bacterium is introduced, or the bacterium may be introduced into a different type of arthropod than the host arthropod from which the *Wolbachia* was isolated.

In some embodiments, the transforming step comprises contacting the bacterium with CRISPR-Cas9 nuclease protein. In some embodiments, the transforming step comprises introducing a nucleic acid encoding a CRISPR-Cas9 nuclease into the bacterium under conditions allowing production of the CRISPR-Cas9 nuclease. In some embodiments, the exogenous nucleic acid is inserted into a capsid gene (e.g., orf7) of the bacterium genome.

In some embodiments, the arthropod is an insect, an arachnid or a crustacean.

In some embodiments, the arthropod is an insect is selected from the group consisting of an Asian citrus psyllid (*Diaphorina citri*), Yellow fever mosquito (*Aedes aegypti*), Potato psyllid (*Bactericerca cockerelli*), German cockroach (*Blatella germanica*, Beg bug (*Cimex lectularius*), fruit fly (*Drosophila melanogaster*), house cricket (*Acheta domesticus*), American grasshopper (*Schistocerca Americana*), tobacco hornworm (*Manduca sexta*) and a red flour beetle (*Tribolium castaneum*).

In some embodiments, the method comprises culturing the bacterium in a host cell before the transforming step. In some embodiments, the host cell is a cell from the same type of arthropod from which the *Wolbachia* was isolated. In some embodiments, the host cell is a cell from a different type of arthropod from which the *Wolbachia* was isolated. In some embodiments, the arthropod is an insect. In some embodiments, the host cell is an insect cell from the same type of insect from which the *Wolbachia* was isolated. In some embodiments, the host cell is an insect cell from a different type of insect from which the *Wolbachia* was isolated. In some embodiments, the host cell is a *Drosophila melanogaster* cell (e.g., an S2 cell).

BRIEF DESCRIPTION OF THE FIGURES

FIG. 1. Verification of wDi in cell culture. The PCR amplification products of the established in vitro wDI infected S2 cells (S2+wDi) and an uninfected (S2) cell line using the general-*Wolbachia* (ftsZ) and the specific-wDi (wsp) primer sets. A molecular size standard (Std) is shown (100 base pair (bp) DNA ladder; NEB). The red markers indicate the 100 bp.

FIG. 2. Intracellular location of wDI in S2 cells. Confocal images of fixed S2 and S2-Di cells, acquired using DAPI (blue) and bright field (bf). DAPI stained the S2 cells nuclei in addition to wDi chromosomes.

FIGS. 3A-3B. Reduction of wDi infection in S2 cells with tetracycline treatment. Infected and uninfected S2 cells with wDi were untreated (control) and treated with tetracycline for three days in S2 medium (A&B). Treatment with tetracycline had no significant effect on S2 cell survival (A). *Wolbachia* FtsZ mean copy number was determined for control and treated samples. wDi infection in S2 cells was reduced by three day of tetracycline treatment (B).

FIG. 4. Purified wDi cells remain viable. wDi cells were extracted and purified from S2 cells and were visualized with the BacLight live-dead stain. wDi cells were stained with green SYTO-9 dye (top row), and dead wDi cells were stained red with Propidium iodine (bottom row) (fluorescent images). For both fluorescent images, the cells were outlined and counted (second column) using ImageI program (analyzed images). There were 2980 total cells, 2853 live cells and 127 dead cells; percent viability of 95.7% and percent mortality of 4.3%. For all subsequent wDi cell extractions and purifications the percent viabilities were >95% (data not shown).

FIGS. 5(A)-5(D). Electroporation of fluorescein-labeled dsRNA on purified wDi. Purified wDi cells were electroporated with fluorescein-labeled dsRNA (dsRNA$^{FL}$). All cells were mixed in with 30 mM dsRNA$^{FL}$ and were imaged at 48 hours-post-electroporation. The control cells that were not electroporated (A), and cells that were electroporated with the highest number of pulses (25×) (B) had no to little dsRNA$^{FL}$ signal. Samples that were electroporated with 18 (C) and 10 (D) pulses had multiple wDi cells with dsRNA$^{FL}$ signal.

FIGS. 6(A)-6(B). Viability of S2+wDi cells after electroporation with pCas9. Cells were counted after two days of reinfection of wDi (A&B). There were two biological replicated for each sample. Control samples were electroporated with no DNA at 18 pulses (A). Electroporation with 1.5 μg of pCas9 had significant effect on viability of S2+wDi (A). *Wolbachia* FtsZ mean copy number was determined for each concentration of pCas9 electroporated (B).

FIGS. 7(A)-7(B). Detection of DNA and protein from pCas9 in S2+dWi$^{pCas9}$ cells. (A) shows that PCR amplification products of pCas9 (primers were designed to amplify a chloramphenicol resistant gene fragment found in plasmid DNA), (L) 100 bp ladder; DNA of samples are from two day post re-infection; #1-8 are samples that were electroporated with pCas9; sample #9 is the electroporation control with no DNA; and sample #10 is the no DNA and no electroporation control. (B) Confocal images of S2+dWi$^{pCas9}$ cells labeled with Cas9 and DAPI. White arrows indicate cytoplasmic wDi that express Cas9.

FIGS. 8(A)-8(B). Strategy of single nucleotide mutation in wDi using homology-directed repair (HDR) with CRISPR/Cas9 system. (A) Nucleotide sequences of wild-type wDi orf7 targeted region, the HRD donor DNA (ssODN) and the resulting mutated wDi orf7. The nucleotide targeted for exchange is highlighted in blue and underlined. (B) Schematic diagram outlining the steps used to transform wDi with either the protein or plasmid base systems in combination with ssODN. Grey circles represent S2 cells, yellow circles represent wDi, and red circles represent transformed wDi cells.

FIGS. 9(A)-9(C). Confirmed point mutation in wDi orf7. wDi cells were transfected with CRISPR/Cas9 components followed by a 48 hours incubation period. DNA was isolated, and the targeted region was amplified and subjected to Sanger sequencing. (A) Depicts experiments conducted with the plasmid base system. (B-C) Depicts experiments conducted with the protein base system; and in (C), 1-3 are technical replicates.

FIGS. 10(A)-10(B). Approach for gene insertion using homology-directed repair with CRISPR/Cas9 system in wDi. (A) Nucleotide sequences of wild-type wDi orf7 targeted region, the homology-directed repair (HRD) plasmid donor DNA (pDonor) and the resulting incorporation of the transgene in wDi. (B) Schematic diagram outlining the steps used to transform wDi with the protein-based system. Grey circles represent S2 cells, yellow circles represent wDi, and green circles represent transformed wDi cells.

FIGS. 11(A)-11(D). Knock-in of GFP in wDi by HDR with CRISPR/Cas9 technology. (A&B) PCR-based genotyping using primer to confirm integration of GFP in wDi cells. Cells electroporated in the absence of pDonor wDi were used as negative controls (CONT). (C) Using FACS, transformed wDi cells were enriched on the basis of GFP intensity (x-axis) after 2d of electroporation. wDi+dsR-NAFlu cells were used as positive controls. Y-axis is the side scatter area (SSC-A). Samples with in the grey area account for GFP+ cells. (D) Wide-field fluorescence microscopy images of live sorted wDi+GFP cells. (E) Confocal miscopy of live S2+wDi+GFP-R cells; samples were stained with Hoechst 33342 (blue).

FIGS. 12(A)-12(G). Insertion of toxin genes in wDi by HDR with CRISPR/Cas9 system. (A) Strategy for toxin gene insertion. Electroporation of wDi was conducted with different pDonors; pCry3Aa, pCry3Aa-R, pCyt2Ca1, pCyt2Ca1-R, pGNA3, or pGNA3-R. (B-G) DNA from transformed and non-transformed negative control (NC) cells were used for PCR analysis. Two biological replicates of each sample are shown. Different PCR primers used in the study: Cry3Aa-f, Cry3Aa-r for Cry3Aa (B), Cry3Aa-R-f, Cry3Aa-R-r for Cry3Aa-R (C), Cyt2Ca1-f, Cyt2Ca1-r for Cyt2Ca1 (D), Cyt2Ca1-R-f, Cyt2Ca1-R-r for Cyt2Ca1-R (E), GNA3-f, GNA3-r for GNA3 (F), and GNA3-R-f, GNA3-R-r for GNA3-R (G).

FIGS. 13(A)-13(C). Vertical transmission of transformed wDi+ in *D. citri*. (A) In vivo visualization of *D. citri* nymphs. Nymph one was injected in the abdominal segment and nymph two was injected twice in the mesothorax with stained Hoechst 33342 (nuclei) wDi+GFP-R. Yellow arrows indicate injection locations. Red arrows indicate exogenous transformed cells that are positive for both nuclei stain and GFP signal. (B&C) Parental *D. citri* were injected with wDi+Cry3Aa-R, their offspring F1 (B) & F3 (C) were individually processed for PCR analysis. (B) Detection of wDi+Cry3Aa-¬R in *D. citri* adults are labeled with green positive symbol and (C) non-wDi+Cry3Aa-R samples were labeled with red negative symbols. Positive and negative DNA controls were used; (+) pDonor DNA and (−) wild-type *D. citri* DNA.

DETAILED DESCRIPTION

The present disclosure is based, in part, on the discovery that *Wolbachia* can be genetically modified via CRISPR technology to express an exogenous nucleic acid of interest.

In one aspect, described herein is a method comprising transforming a *Wolbachia* bacterium with an exogenous nucleic acid using a CRISP-Cas9 nuclease to insert the nucleic acid into the genome of the bacterium, thereby producing a genetically transformed bacterium; and introducing the genetically transformed bacterium into an arthropod. In some embodiments, the method comprises isolating the *Wolbachia* bacterium from a host arthropod before the transforming step.

The term "exogenous nucleic acid" is a nucleic acid that is not normally present in a particular host cell. The term "exogenous nucleic acid" as used herein refers to a nucleic acid that is not present in the wild-type *Wolbachia* genome. The *Wolbachia* bacterium has been "genetically modified" or "transformed" or "transfected" by exogenous nucleic acid when such nucleic acid(s) has been introduced inside the cell.

Nucleic acids include DNA and RNA; can be single- or double-stranded; can be linear, branched or circular; and can be of any length. Methods for the introduction of exogenous molecules into cells are known to those of skill in the art and include, but are not limited to, lipid-mediated transfer (i.e., liposomes, including neutral and cationic lipids), electroporation, calcium phosphate precipitation, polyethyleneimine (PEI)-mediated transfection, direct injection, cell fusion, nanoparticle-mediated nucleic acid delivery (including lipid nanoparticles (LNP)), particle bombardment (e.g., particle gun technology), calcium phosphate co-precipitation, DEAE-dextran-mediated transfer and viral vector- or bacteriophage-mediated transfer. A general discussion of these methods can be found in Ausubel, et al., Short Protocols in Molecular Biology, 3rd ed., Wiley & Sons, 1995. It will be appreciated that the methods described herein are suitable for introducing any exogenous nucleic acid (e.g., encoding a toxin, encoding Cas9 nuclease, or encoding guide RNA) into a host cell.

Exogenous nucleic acids are typically introduced into host cells using an expression vector. Contemplated expression vectors include, but are not limited to, plasmids, bacteriophage-based vectors, and viral vectors, such as viral vectors based on vaccinia virus, poliovirus, adenovirus, adeno-associated virus, SV40, herpes simplex virus, human immunodeficiency virus, retrovirus (e.g., Murine Leukemia Virus, spleen necrosis virus, Rous Sarcoma Virus, Harvey Sarcoma Virus, avian leukosis virus, a lentivirus, human immunodeficiency virus, myeloproliferative sarcoma virus, and mammary tumor virus). Other vectors may be used so long as they are compatible with *Wolbachia*.

In some embodiments, the exogenous nucleic acid encodes a toxin. Exemplary toxins include, but are not limited to, *Bacillus thuringiensis* crystal toxin (Cry3Aa), *Bacillus thuringiensis* cytolytic toxin (Cyt2Ca1) and *Galanthus nivalis* agglutinin (GNA3) and ponericins. In some embodiments, the exogenous nucleic encodes a peptide. Exemplary peptides include, but are not limited to gut-binding peptides, and insecticidal peptides (e.g., snowdrop lectin (GNA, scorpion venom toxi and indolicidin). Alternatively (or in addition), the bacterium genome is modified to include an exogenous nucleic acid encoding a selectable marker.

In various aspects, the exogenous nucleic acid is inserted into a region of the *Wolbachia* genome that (1) does not kill the bacterium and (2) allows for the production of a protein encoded by the exogenous nucleic acid. Optionally, the exogenous nucleic acid is inserted into the capsid protein gene, orf7, such as a unique genomic site adjacent to the protospacer adjacent motif (PAM) sequence found in orf7. Expression of the exogenous nucleic acid may be driven by an endogenous (native) promoter in the *Wolbachia* genome, although the use of exogenous promoters also is contemplated. In any event, the exogenous nucleic acid is preferably "operably linked" to regulatory sequence(s) in a manner that allows for expression of the nucleotide sequence. The term "regulatory sequence" is intended to include, for example, promoters, enhancers and other expression control elements (e.g., polyadenylation signals). Such regulatory sequences are well known in the art and are described, for example, in Goeddel; Gene Expression Technology: Methods in Enzymology 185, Academic Press, San Diego, Calif. (1990).

In some embodiments, the *Wolbachia* bacterium is isolated from an arthropod host. Additionally, the genetically transformed *Wolbachia* bacterium optionally serves as a vector for delivering an exogenous protein (by way of the exogenous nucleic acid embedded in the bacterial genome) to an arthropod host. As used herein, the term "arthropod" refers to an invertebrate animal that is characterized by a chitinous exoskeleton and a segmented body with paired, jointed appendages (e.g., legs or feet). Accordingly, an arthropod may be, but is not limited to, an insect (e.g., a mosquito or a fly), a crustacean (e.g., a prawn, a crab or a lobster), or an arachnid (e.g., a tick or a mite). As also used herein, the terms "arthropod vector" or "arthropod vector population" refer to an arthropod, or a population thereof, that is capable of transmitting a pathogen from one host to another.

Insects include insects of orders such as Diptera (e.g., mosquitoes, horseflies, midges, stableflies and tsetse flies), Phthiraptera (e.g., lice), Siphonaptera (e.g., fleas) and Hemiptera (e.g., bedbugs and triatomine bugs). In some embodiments, the insect is selected from the group consisting of an Asian citrus psyllid (*Diaphorina citri*), Yellow fever mosquito (*Aedes aegypti*), Potato psyllid (*Bactericerca cockerelli*), German cockroach (*Blatella germanica*, Beg bug (*Cimex lectularius*), fruit fly (*Drosophila melanogaster*), house cricket (*Acheta domesticus*), American grasshopper (*Schistocerca Americana*), tobacco hornworm (*Manduca sexta*) and a red flour beetle (*Tribolium castaneum*).

An example of an arachnid is a tick or mite (e.g., of the families Argasida, Trombidiidae and Ixodidae). An example of a crustacean is a prawn or a crab (e.g., of the families Peneidae and Coenobitidae, such as *Penaeus monodon, Marsupenaeus japonicus* and *Litopenaeus vannamei*).

In some embodiments, the genetically transformed *Wolbachia* bacterium is capable of modifying one or more biological properties of an arthropod host. For example, in some embodiments, the method described herein introduces a reproductive abnormality in an arthropod host such as, but not limited to, parthenogenesis, feminization, male killing, and cytoplasmic incompatibility (CI). Typically, according to this embodiment, the reproductive abnormality reduces fecundity within an arthropod vector population. As used herein, the term "fecundity" refers to the ability of an arthropod, or a population thereof, to reproduce.

Isolation of *Wolbachia*

In various aspects, the method described herein comprises the step of isolating *Wolbachia* from a host arthropod. In some embodiments, the *Wolbachia* is isolated from Asian citrus psyllid (*Diaphorina citri*). The term "*Wolbachia*" as used herein is meant to include all strains of bacteria under the genus *Wolbachia*. Exemplary strains of *Wolbachis* include, but are not limited to, rains such as wDi, wMel, wMelPop, wMelPop-CLA, wMelCS, wAu, wRi, wNo, wHa, wMau and wCer2.

The *Wolbachia* bacterium can be isolated from the host arthropod by any method known in the art. In some embodiments, the *Wolbachia* is isolated as described in Example 1.

Once isolated, the *Wolbachia* is cultured in a suitable host cell. A "host cell," as used herein, denotes an in vivo or in vitro prokaryotic cell (e.g., bacterial or archaeal cell), eukaryotic cell, or a cell from a multicellular organism (e.g., a cell line) cultured as a unicellular entity, which eukaryotic or prokaryotic cells can be, or have been, used as recipients for a nucleic acid, and include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. In some embodiments, the host cell is a cell from the same type of arthropod from which the *Wolbachia* was isolated. In some embodiments, the host cell is a cell from a different type of arthropod from which the *Wolbachia* was isolated.

In some embodiments, the host cell is an insect cell. In some embodiments, the host cell is an insect cell from the same type of insect from which the *Wolbachia* was isolated. In this regard, for example, the host cell could be a *D. citri* cell and the *Wolbachi* is isolated from *D. citri*. In some embodiments, the host cell is an insect cell from a different type of insect from which the *Wolbachia* was isolated. In this regard, for example, the host cell is a *Drosophila melanogaster* cell and the *Wolbachia* is isolated from *D. citri*.

In some embodiments, the insect cell is a *Drosophila melanogaster* cell, such as an S2 cell. In some embodiments, the *Wolbachia* bacterium is cultured in an S2 cell line in Schneider medium, optionally under the conditions described in Example 1.

To aid in identification of insect cells comprising *Wolbachia*, the modified *Wolbachia* may be further manipulated to include a selectable marker gene that is functional in bacteria. Useful selectable markers include, but are not limited to, enzymes which provide for resistance to an antibiotic such as Ampicillin resistance gene (Amp$^r$), a tetracycline resistance gene (Tc$^r$), a Cycloheximide-resistance L41 gene, the gene conferring resistance to antibiotic G418 (such as the APT gene derived from a bacterial transposon Tn903), the antibiotic Hygromycin B-resistance gene, a Gentamycin resistance gene, and/or a kanamycin resistance gene, among others. Similarly, enzymes providing for production of a compound identifiable by color change (such as GUS) or luminescence (such as luciferase) are included herein.

CRISPR Endonuclease System

A CRISPR (Clustered Regularly Interspaced Short Palindromic Repeats) genomic locus can be found in the genomes of many prokaryotes (e.g., bacteria and archaea). In prokaryotes, the CRISPR locus encodes products that function as a type of immune system to help defend the prokaryotes against foreign invaders, such as virus and phage. There are three stages of CRISPR locus function: integration of new sequences into the locus, biogenesis of CRISPR RNA (crRNA), and silencing of foreign invader nucleic acid. Five types of CRISPR systems (e.g., Type I, Type II, Type III, Type U, and Type V) have been identified.

A CRISPR locus includes a number of short repeating sequences referred to as "repeats." The repeats can form hairpin structures and/or comprise unstructured single-stranded sequences. The repeats usually occur in clusters and frequently diverge between species. The repeats are regularly interspaced with unique intervening sequences referred to as "spacers," resulting in a repeat-spacer-repeat locus architecture. The spacers are identical to or have high homology with known foreign invader sequences. A spacer-repeat unit encodes a crisprRNA (crRNA), which is processed into a mature form of the spacer-repeat unit. A crRNA comprises a "seed" or spacer sequence that is involved in targeting a target nucleic acid (in the naturally occurring form in prokaryotes, the spacer sequence targets the foreign invader nucleic acid). A spacer sequence is located at the 5' or 3' end of the crRNA.

A CRISPR locus also comprises polynucleotide sequences encoding CRISPR Associated (Cas) genes. Cas genes encode endonucleases involved in the biogenesis and the interference stages of crRNA function in prokaryotes. Some Cas genes comprise homologous secondary and/or tertiary structures.

crRNA biogenesis in a Type II CRISPR system in nature requires a trans-activating CRISPR RNA (tracrRNA). The tracrRNA is modified by endogenous RNaseIII, and then hybridizes to a crRNA repeat in the pre-crRNA array. Endogenous RNaseIII is recruited to cleave the pre-crRNA. Cleaved crRNAs are subjected to exoribonuclease trimming to produce the mature crRNA form (e.g., 5' trimming). The tracrRNA remains hybridized to the crRNA, and the tracrRNA and the crRNA associate with a site-directed polypeptide (e.g., Cas9). The crRNA of the crRNA-tracrRNA-Cas9 complex guides the complex to a target nucleic acid to which the crRNA can hybridize. Hybridization of the crRNA to the target nucleic acid activates Cas9 for targeted nucleic acid cleavage. The target nucleic acid in a Type II CRISPR system is referred to as a protospacer adjacent motif (PAM). In nature, the PAM facilitates binding of a site-directed polypeptide (e.g., Cas9) to the target nucleic acid. Type II systems (also referred to as Nmeni or CASS4) are further subdivided into Type II-A (CASS4) and II-B (CASS4a). Jinek et al., Science, 337(6096):816-821 (2012) showed that the CRISPR/Cas9 system is useful for RNA-programmable genome editing, and International Patent Application Publication Number WO2013/176772 (incorporated herein by reference) provides numerous examples and applications of the CRISPR/Cas endonuclease system for site-specific gene editing.

Exemplary CRISPR/Cas polypeptides include the Cas9 polypeptides in FIG. 1 of Fonfara et al., Nucleic Acids Research, 42: 2577-2590 (2014) (incorporated herein by reference). The CRISPR/Cas gene naming system has undergone extensive rewriting since the Cas genes were discovered. FIG. 5 of Fonfara, supra, provides PAM sequences for the Cas9 polypeptides from various species.

Cas9 polypeptides can introduce double-strand breaks or single-strand breaks in nucleic acids, e.g., genomic DNA. The double-strand break can stimulate a cell's endogenous DNA-repair pathways (e.g., homology-dependent repair (HDR) or non-homologous end joining (NHEJ) or alternative non-homologous end joining (A-NHEJ) or microhomology-mediated end joining (MMEJ)). NHEJ can repair cleaved target nucleic acid without the need for a homologous template. This can sometimes result in small deletions or insertions (indels) in the target nucleic acid at the site of cleavage, and can lead to disruption or alteration of gene expression. HDR can occur when a homologous repair template, or exogenous nucleic acid, is available.

Thus, in some cases, homologous recombination is used to insert an exogenous nucleic acid into the genome of the *Wolbachia* bacterium. The modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. The processes of deleting genomic DNA and integrating non-native nucleic acid into genomic DNA are examples of genome editing.

In some aspects, the Cas9 nuclease is introduced to the *Wolbachia* as a protein (i.e., a protein-based system). Typically, the *Wolbachia* is treated chemically, electrically, or mechanically to allow Cas9 nuclease entry into the cell. Alternatively, the Cas9 nuclease is introduced to the *Wolbachia* as a nucleic acid (e.g., DNA or mRNA) under conditions which allow production of the nuclease. Guide RNA also is introduced into the *Wolbachia*.

A genome-targeting RNA is referred to as a "guide RNA" or "gRNA" herein. A guide RNA comprises at least a spacer sequence that hybridizes to a target nucleic acid sequence of interest, and a CRISPR repeat sequence. In Type II systems, the gRNA also comprises a tracrRNA sequence. In the Type II guide RNA, the CRISPR repeat sequence and tracrRNA sequence hybridize to each other to form a duplex. The duplex binds a site-directed polypeptide, such that the guide RNA and site-direct polypeptide form a complex. The guide RNA provides target specificity to the complex by virtue of its association with the Cas9 nuclease. The guide RNA thus directs the activity of the Cas9 nuclease. In some embodiments, the guide RNA is a single molecule guide RNA (sgRNA).

A single-molecule guide RNA in a Type II system comprises, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may comprise elements that contribute additional functionality (e.g., stability) to the guide RNA. The single-molecule guide linker links the minimum CRISPR repeat and the minimum tracrRNA sequence to form a hairpin structure. The optional tracrRNA extension comprises one or more hairpins.

Exemplary sgRNA for use in the methods described herein include, but are not limited to, the sgRNAs provided in Table 2 in Example 2.

A nucleic acid encoding the Cas9 nuclease and/or guide RNA is typically delivered in an expression vector. The exogenous nucleic acid can be delivered in the same vector as the Cas9 nucleic acid, or in a second vector. Any of the expression vectors described herein may be used to deliver Cas9 nuclease-encoding nucleic acid into the *Wolbachia*; in many aspects, the expression vector is a plasmid. In some embodiments, an expression vector comprises one or more transcription and/or translation control elements. Depending on the host/vector system utilized, any of a number of suitable transcription and translation control elements, including constitutive and inducible promoters, transcription enhancer elements, transcription terminators, etc., may be used The Cas9 nuclease-encoding nucleic acid is operably linked to a promoter that drives protein expression. Exemplary prokaryotic promoters include, but are not limited to, wMel WSP Promote, wDc WSP Promoter and T7. For expressing small RNAs, including guide RNAs used in connection with Cas or Cpf1 endonuclease, promoters such as RNA polymerase III promoters, including for example U6 and H1, can be advantageous. Suitable promoters, as well as parameters for enhancing the use of such promoters, are known in art, and additional information and approaches are regularly being described; see, e.g., Ma, H. et al., *Molecular Therapy—Nucleic Acids* 3, e161 (2014) doi:10.1038/mtna.2014.12.

In some aspects, the genetically-modified bacterium is introduced into an arthropod. Optionally, an infected arthropod demonstrates a reproductive abnormality, such as an abnormality described herein, resulting in a reduction in pest fecundity. The genetically-modified bacterium may be introduced into arthropod using any suitable technique, such as a shell vial technique or a microinjection. In some embodiments, the genetically-transformed bacterium is introduced by microinjection into an abdominal segment of the mesothorax (e.g., the ventral first abdominal segment of the mesothorax). In some embodiments, the genetically-transformed bacterium is injected into the dorsal side of the mesothorax. In some embodiments, the genetically-transformed bacterium is electroporated into eggs of an arthropod. In some embodiments, the genetically-transformed bacterium is incorporated into the diet of a target insect and fed to the target insect.

The *Wolbachia* platform has the potential for ubiquitous use among insects. In some embodiments, the genetically-modified bacterium is modified to express genes that will interfere with reproduction, alter metabolic function, transmission of animal and plant pathogens (e.g. viruses, bacteria, *Plasmodium*), bactericides, insect toxins, and or dsRNA (for RNAi management). In some embodiments, the *Wolbachia* platform is used to disrupt *Candidatus liberibacter asiaticus* (Clas) replication and multiplication. Exemplary target mechanisms are set forth below in Table 1.

TABLE 1

Targets for disruption of Clas replication and multiplication

| Potential target mechanism | Gene |
| --- | --- |
| Knock-out of wDi gene, facilitates survival of CLas in *D. citri* | Holin promoter repressor protein |
| Knock-in of Profftella gene in wDi, mediates Clas | Polyketicle diaphorin |
| Knock-in genes from wDi, downregulated in ACP infected with CLas | Iron deficiency-induced protein A<br>Ankyrin<br>Membrane protein<br>Polynucleotide phosphorylase<br>Ribosomal proteins<br>Phosphoribosylamine-glycine ligase<br>Thioredoxin |
| Knock-in genes from ACP gut downregulated in ACP infected with Clas | Cathepsin B<br>Lipase<br>Facilitated trehalose transporter |
| Knock-out or -down genes from gut, upregulated in *D. citri* infected with Clas | Cysteine proteases<br>Mucin |
| Knock-in genes from *D. citri* immune system, downregulated in *D. citri* infected with Clas | Basement membrane-specific heparan sulfate proteoglycan core protein<br>Heat-shock proteins<br>Transferrin-like transcripts |
| Knock-in genes from the ACP gut mitochondria, downregulated in *D. citri* infected with Clas | Enzymes regulating metabolic flux during the TCA cycle |

All of the U.S. patents, U.S. patent application publications, U.S. patent applications, foreign patents, foreign patent applications and non-patent publications referred to in this specification, are incorporated herein by reference, in their entireties.

From the foregoing it will be appreciated that, although specific embodiments of the invention have been described herein for purposes of illustration, various modifications may be made without deviating from the spirit and scope of the invention.

EXAMPLES

Example 1—Isolation of *Wolbachia* from *Diaphorina citri*

Preparations of *Wolbachia* from *Diaphorina citri* (wDi): The *Diaphorina citri* were collected from Lake Alfred, Fla. The cell line was established following methods described previously with modifications (O'Neill, et al., 1997). Psyllids were placed on a sterile diet rings for two days prior to *Wolbachia* extraction. Individual psyllids were surface sterilized by immersion in 10% bleach (Fisher Scientific, Fair Lawn, N.J.) for five minutes and followed by 70% ethanol (Fisher Scientific, Fair Lawn, N.J.) wash for one minute. Psyllids were rinsed twice with filtered sterile deionized water. Individual psyllids were transferred in an 1.5 mL microcentrifuge tube containing 1 mL of Schneider's *Drosophila* (S2) media (Gibco, Carlsbad, Calif.). Psyllids were homogenized with a pellet pestle. The resulting suspension was centrifuged at 100×g for five minutes. The supernatant was placed into a new 1.5 mL microcentrifuge tube. The supernatant was centrifuged at 400×g for five minutes. The supernatant was removed and the pellet was resuspended with 1 mL of S2 media. The samples were centrifuged at 100×g for five minutes, then the supernatant was transferred to a new 1.5 mL microcentrifuge tube. The supernatant was centrifuged at 4000×g for five minutes, finally the pellet was resuspended in 1 mL of S2 media.

Infection of wDi in S2 cells: S2 cells (Invitrogen, Carlsbad, Calif.) were placed in a 24-well plate and were seeded at a density of $4.0 \times 10^5$ cells per well in a total of 1 mL of S2 media containing 10% heat inactivated fetal bovine serum, 50 units of penicillin (Sigma, St. Louise, Mo.) and 50 μg streptomycin sulfate (Gibco, Grand Island, N.Y.) per mL (S2 complete media). S2 cells ($2.0 \times 10^5$) were collected in 1.5 mL microcentrifuge tubes. Cells were centrifuged at 1000×g for three minutes. An individual psyllid-*Wolbachia* (wDi) extraction was used to resuspend one tube of pelleted S2 cells. Then samples were centrifuged at 2500×g for one hour at 15° C. The pelleted cells were resuspended with 1 mL of S2 complete media and added into a sterile 25-cm2 flask containing 4 mL of S2 complete media. Hereafter, the cells were kept at 28° C. After two days, the cells were transferred to a 75-cm² flask with 4 ml of S2 complete media. The wDi-infected (S2+wDi) and uninfected-S2 cells were maintained according to standard procedures (Baum and Cherbas, 2008).

Diagnostic PCR to screen wDi infection in cell culture: DNA was extracted from cell culture using the DNeasy Blood and Tissue Kit (Qiagen, Valencia, Calif.). The concentration and purity of DNA was quantified by using NanoDrop 2000 spectrophotometer (ThermoFisher Scientific, Wilmington, Del.). The wsp (*Wolbachia* outer surface protein) and ftsZ (an essential cell division protein in *Wolbachia*) genes were amplified by diagnostic PCR using the GoTaq Colorless Master Mix (Promega, Madison, Wis.) in a T100 thermal cycler (Bio-Rad, Foster City, Calif.). The wDi wsp (wsp Forward: AGG GCT TTA CTC AAA ATT GG (SEQ ID NO: 1) and wDi wsp Reverse: CAC CAA CGGT ATG GAG TGA TAG G (SEQ ID NO: 2)), and the *Wolbachia* ftsZ (ftsZ Forward: ACG AGC CAG AGA AGC AAG AG (SEQ ID NO: 3) and ftsZ Reverse: TAC GTC GCA CAC CTT CAA AA (SEQ ID NO: 4)) (Dossi et al., 2014) primers were used for detection of *Wolbachia* under the following conditions: one cycle of 95° C. for 3 m, followed by 34 cycles of 95° C. for 30 s, 55° C. for 30 s, 72° C. for 1 m, and a final extension cycle of 72° C. for 5 m. Amplification products were separated on an 1.5% agarose (Fisher Chemical, Fair Lawn, N.J.) gel.

Localization of wDi in S2 cells: Coverslips were washed with 80% ethanol and then coated with concavalin A (Vector Labs, Burlingame, Calif.) to assist cell adhesion to coverslip (Buster et al., 2010). Individual coated coverslips were places in 35×10 mm² tissue culture dishes with 1 mL of S2 media. At a concentration of $1.5 \times 10^6$ cells/mL, 150 μL of cell suspension were added to individual coverslips, and were allowed to adhere for one hour at room temperature. The S2 media was removed and coverslips were gently washed with 1×PBS (Fisher Scientific, Fair Lawn, N.J.) for five minutes. Cells were fixed in 4% paraformaldehyde (Electron Microscopy Sciences, Hatfield, Pa.) for one hour at room temperature. Following fixation, samples were washed three times for five minutes with 1×PBS at room temperature. Then coverslips were mounted on microscope slides with VECTSHIELD antifade mounting medium with DAPI (Vector Laboratories, Burlingame, Calif.). Slides were images with a confocal microscope (Leica SP8 Laser-scanning Confocal).

Tetracycline treatment on wDi infected cell line: Tetracycline treatment was used to clear wDi infection from cell culture. Uninfected S2 and infected S2+wDi cell lines were divided into two separate 75 cm² flasks. The control samples were grown in S2 complete media, and the treated samples were grown in S2 complete media supplemented with 0.1 mg/mL tetracycline (Sigma, St. Louis, Mo.). Three biological replicates were conducted. Cells were left in treatment for three days. After three days of treatment, survival of S2 and S2+wDi cells were obtained by using trypan blue stain and Countess II FL Automated Cell Counter (Invitrogen, Eugene, Oreg.). In addition, DNA was extracted by the DNeasy Blood and Tissue Kit (Qiagen, Valencia, Calif.), and quantified by using a NanoDrop 2000 spectrophotometer (ThermoFisher Scientific, Wilmington, Del.). DNA samples were subjected to quantitative real-time PCR analysis (qRT-PCR) to determine *Wolbachia* (ftsZ) copy numbers. qRT-PCR was performed using SYBR Green PCR Master Mix (Applied Biosystems, Woolston, Wargton, UK) following the manufacturer protocol. For each sample, 50 ng/μl of DNA were used in for qRT-PCR analysis. The construction of the standard curve template DNA (ftsZ gene), and the subsequent steps for qRT-PCR were conducted as described in Chu et al. (2016).

Extraction and purification of wDi from S2 cells: Extraction and purification of wDi was conducted as previously described by Gamston and Rasgon (2007). Infected S2 cells with wDi were grown in 75-cm² culture flasks in 40 mL S2 complete media to approximately 90% confluence. Cells were dislodged into the media by taping the flask, scraping the flask surface and by pipetting. The cells were harvested in 50 mL centrifuge tubes. To lyse the cells, approximately 5 mL of sterile 3 mm borosilicate glass beads were added to each sample and were vortexed at the highest speed for five minutes at room temperature (RT). The supernatant (containing S2 and wDi cells) was transferred into a clean and sterile 50 mL centrifuge tube. The supernatant was centrifuged at 2500×g for ten minutes at 4° C. The supernatant was gently filtered through a sterile 5 μm filter syringe (Whatman, Little Chalfont, Buckinghamshire, UK) and collected in a high-speed centrifuge tube. Samples were centrifuged at 18000×g at 4° C. for ten minutes. The supernatant was removed. The pellet containing wDi was resuspended with 2 mL of S2 complete media. Samples were gently purified with 2.7 μm filter syringes (Whatman, Little Chalfont, Buckinghamshire, UK) into a long-term storage tube. Purified wDi were held in suspension in S2 complete media at room temperature up to five days.

Viability Assays: S2 cells were counted on an automated cell counter, Countess II FL (Invitrogen, Eugene, Oreg.) with trypan blue staining (Invitrogen, Eugene, Oreg.) following manufactures protocol. The viability of purified wDi was assayed by LIVE/DEAD BacLight Bacterial Viability and Counting Kit (Invitrogen, Eugene, Oreg.) following manufacturer's protocol and using the Countess II FL Automated Cell Counter (Invitrogen, Eugene, Oreg.).

Transformation of purified wDi. The transformation method of wDi was modified from Rachek et al. (1998). For each electroporated sample, $5.0 \times 10^5$ of wDi cells were used. Isolated wDi were centrifuged at 1000×g at 15° C. for ten minutes. Supernatant was removed and cells were resuspended with 100 μL of 250 mM sucrose (Sigma, St. Louis, Mo.). Samples were centrifuged once more at 1000×g at 15° C. for ten minutes. The supernatant was removed and cells were resuspended with 50 μL of 250 mM sucrose (Sigma, St. Louis, Mo.) per electroporated sample. For the initial visualization of electroporated wDi, the 50 μL samples of wDi suspension were mixed with 10 mM or 30 mM fluorescein-labeled dsRNA (dsRNAFL) oligomer (BLOCK-iT Fluorescent Oligo, Invitrogen, Carlsbad, Calif.). After establishing the electroporation conditions, samples were electroporated with the plasmid constructed by Jiang et al. (2013) (Addgene plasmid #42876), pCas9. Plasmid was prepared following standard cloning techniques (Sambrook and Russell, 2001). Plasmids were purified with a PureLink HiPure Plasmid Midiprep Kit by Invitrogen (Vilnius, Lithuania). The 50 µL samples of wDi suspension were mixed with 0.5, 1.0 or 1.5 m of circular plasmid DNA (pCas9). Samples were transferred to a 0.1-cm gap electroporation cuvette (BTX Harvard Apparatus, Holliston, Mass.) and chilled on ice for ten minutes. The cuvette was placed in a BTX Harvard Apparatus Electro Square Porator (ECM 830) (Holliston, Mass.) and electroporated (voltage at 1.7 kV, pulse length at 176 us, pulse intervals at 100 ms, and number of pulses at 18 times). Cells were placed in a 24-well plate suspended in 500 mL of Hank's Balance Salts (HBS) solution at RT. For samples electroporated with dsRNAFL, plates were covered with foil paper to protect from light. Electroporated cells were allowed to recover for two days.

After two days of recovery, cells were collected and placed in 1.5 mL microcentrifuge tubes. Cells were centrifuged at 2000×g for ten minutes. The pellets were resuspended with 200 µL 1× phosphate buffered saline (PBS). Cells electroporated with dsRNAFL were mounted on a slide and screened under a fluorescent microscope (Olympus BX61 Epifluorescence microscope). Cells electroporated with pCas9 were centrifuged at 10000×rpms for ten minutes. Pellets were resuspended with 50 µL water. Resuspended cells were mixed with RQ1 DNase (Promega) to remove extracellular DNA. The mix samples were incubated at 37° C. for one hour. After, samples were centrifuged at 10000× rpms for ten minutes. The pellets were then resuspended with 500 mL of S2 complete media. Electroporated wDi were re-introduce in S2 cells ($6.0 \times 10^5$ cell per sample) as described above. To detect pCas9 from cells, DNA was extracted from cell culture to amplify a segment of the chloramphenicol resistant gene found in the pCas9 by PCR as described above. The forward (GCA GTC GGA TAC CTT CCT ATT C—(SEQ ID NO: 5)) and reverse (TCC CTG ATG GTC GTC ATC TA—(SEQ ID NO: 6)) primers were used to detect the plasmid in S2+wDipCas9 DNA samples.

Immunocytochemistry: Immunocytochemistry was performed to visualize the Cas9 protein in S2+wDipCas9 cells. Preparation of cells onto coverslips was conducted as previously describe above. After fixation washes with PBS, an additional wash was conducted with 1×PBS-TritonX-100 (0.5% T) for five minutes at room temperature. Samples were blocked with 5% BSA for one hour at room temperature. Blocking solution was removed, then samples were incubated with anti-CRISPR-Cas9-Alexa Fluor 488 (1:500, Novus Biologicals, Littleton, Colo.) for one hour at room temperature. Antibody solution was removed and samples were washed with 1×PBS three times for five minutes at room temperature. Samples were mounted with VECTSHIELD antifade mounting medium with DAPI (Vector Laboratories, Burlingame, Calif.). Samples were imaged with a confocal microscope (Leica SP8 Laser-scanning Confocal).

Infection of S2 cells: Infections were established by centrifugation of infected host material (adult *D. citri*) onto an uninfected *D. melanogaster* Schneider's (S2) cells. This founded a continuous culture of S2 infected wDi cell line (S2+wDi). The presence of wDi infection in the S2 line was confirmed by diagnostic polymerase chain reaction (PCR) assay using primers for the general *Wolbachia* ftsZ and the specific wDi outer surface protein (wsp) genes (FIG. 1). Only S2 cells that were infected with wDi had amplification of *Wolbachia* DNA, while S2 only cells had no amplification for *Wolbachia* DNA. To visualize wDi in S2 cells, cells were fixed on concanavalin A slides and mounted with a mounting medium containing DAPI (Buster et al., 2010). Confocal microscopy revealed that wDi localizes intracellularly in S2 cells (FIG. 2).

The treatment of tetracycline has been previous shown to eliminate *Wolbachia* infection (Dobson et al., 2002). To verify the wDi DNA was amplified from living bacteria and not residual exogenous DNA, the S2+wDi cells were divided into two parts; one treated with tetracycline and the other remained untreated (control). Treatment with tetracycline, had no effect on uninfected S2 cells' and S2+wDi cells' survival (FIG. 3A), and a drastic reduction of wDi cell density was observed in treated S2+wDi cells (FIG. 3B).

Extraction and purification of wDi: Gamston and Rasgon (2007) demonstrated that *Wolbachia* can be isolated and viable for one week outside its host cell, the *Aedes albopictus* embryonic cell line. Thus, large volumes of the established S2+wDi cells were grown for extraction and isolation of wDi cells as previously described by Gamston and Rasgon (2007). After purification of wDi, cells were maintained is S2 complete medium at room temperature and were stained with BacLight alive-dead stain to assess their viability. BacLight alive-dead stain uses two dyes SYTO-9 to stain live and dead cell membranes green, and Propidium iodide to stain cells with compromised cell membranes red (FIG. 4). Each fluorescent cell was counted, and all wDi cell samples reported in this study that were isolated and purified remained viable with >95% viability after two day post isolation.

Transformation of purified wDi: For optimization purposes, multiple numbers of pulses (i.e., 25, 18, and 10) were tested. To visualize the exogenous nucleotides, 10 mM and 30 mM of a fluorescein-labeled dsRNA (dsRNAFL) oligomer (BLOCK-iT Fluorescent Oligo) was electroporated. Samples were analyzed at 48 hours-post-electroporation. Samples electroporated with 10 mM had little to no positive wDi cells (data not shown). However, samples electroporated with 30 mM had dsRNAFL signal in wDi cells (FIG. 5B-D). Samples with 25 pulses had very little dsRNAFL signal in cells (FIG. 5B); while, samples with 18 and 10 pulses had dsRNAFL signal in various wDi cells (FIGS. 5C & D).

After transformation of wDi, the purified/transformed wDi was introduced into a host cell to demonstrate that it is viable in host cells after transformation and that it can express an exogenous protein. Thus, we electroporated a CRISPR-Cas plasmid for bacterial expression of Cas9 nuclease, pCas9 (Jiang W et al., 2013). After two days of electroporation with pCas9, wDi cells were harvested and treated with RQ1 DNase (Promega) to remove extracellular plasmid. Next, the transformed wDi cells were mixed with uninfected S2 cells and centrifuged to create S2+wDipCas9 cells. Viability of re-infected S2 cells with control wDi (no DNA; 18 pulses electroporation) was 95% for both biological replicates (FIG. 6A: Control); while, viability was drastically reduced for samples electroporated with the highest pCas9 concentration (1.5 m). The samples electroporated with 0.5 and 1.0 µg of pCas9 had no effect on S2+wDipCas9 cells' viability independent of electroporated pulse number (FIG. 6A). In addition, the density of wDi was the highest in these two samples that were electroporated with 18 pulses (FIG. 6B).

The confirmation of transformed wDi in S2 cells was followed by detecting the acquisition of pCas9 DNA and the production of the Cas9 protein in the S2+wDipCas9 samples. The intracellular plasmid was detected by PCR (FIG. 7A) and protein expression of Cas9 was detected my immunofluorescence (FIG. 7B). Two days post re-infection of S2 with wDipCas9, cells were processed for DNA extraction and immunostaining using anti-Cas9. Amplification of the chloramphenicol resistant gene found in pCas9 was detected in S2+wDipCas9 samples by PCR (FIG. 7A). In addition, protein expression of Cas9 was localized in wDi cells found within the host cell (FIG. 7B).

The foregoing Example described the isolation of wDi from the S2 cells and their ability to survive outside the host cell up to one week, which provided a window of opportunity to introduce pCas9 into wDi using an in vitro culture system.

Example 2—Bioengineering of *Wolbachia* Using CRISPR/Cas9

The following Example describes the genetic modification of *Wolbachia* by both plasmid-based and protein-based CRISPR-Cas9 systems.

Insects: An uninfected *Diaphorina citri Kuwayama* population was established in 2005, at the University of Florida Citrus Research and Education Center (UF-CREC, Lake Alfred Fla., USA), from a field population collected in Polk Co. (28.0' N, 81.9' W) before detection of Huanglongbind in Florida. *Candidatus liberibacter asiaticus* (CLas) infected *D. citri* were reared in infected *Citrus sinensis* (L.) Osb. plants. Both *D. citri* colonies were kept in a secure quarantine facility in the UF-CREC (Lake Alfred, Fla.). All experiments were conducted in a growth chamber at 28° C., 16:8 h light:dark photoperiod cycle and 60-80% relative humidity.

Insect cell line: Schneider's *Drosophila* (S2) cells infected with the *Wolbachia* strain from *D. citri* (wDi) (S2+wDi) and uninfected S2 cells were acquired and maintained as described in Example 1. Growth media used was a mixture of S2 media containing 10% heat inactivated fetal bovine serum, 50 unit of penicillin and 50 μg streptomycin sulfate per mL (S2 complete media).

Target region for genome engineering in wDi: Selected sgRNAs located in the phage capsid protein gene (orf7) (WDIAC_RS06650 annotated on the Contig75.1; GenBank accession number NZ_AMZJO1000095.1) were analyzed using the draft genome of wDi. The sgRNA selected for the experiments was predicted to target a unique genomic site adjacent to the protospacer adjacent motif (PAM) sequence found in orf7.

Plasmid encoded- and recombinant CRISPR-Cas9: For the plasmid based system, pCas9 was purchased from Addgene (plasmid 42876, donated by Luciano Marraffini). To introduce the single guide RNA (sgRNA) into the plasmid, single-stranded oligonucleotides (Integrated DNA Technologies) containing the spacers were phosphorylated, annealed and ligated as previously described by Jiang et al (2013). The spacer sequences are listed in Table 2. For the protein based system, GeneArt™ Platinum™ Cas9 Nuclease and GeneArt™ Precision gRNA Synthesis Kit were purchased and prepared as described by the manufacturer (Therma Fisher Scientific). The DNA oligonucleotides used for sgRNA synthesis are listed in Table 2.

TABLE 2

| sgRNA DNA synthesis oligos. | |
|---|---|
| orf7 spacer for cloning in pCas9 | 5'-AAACATAAATTCTCCTATTTTCT CG-3' (SEQ ID NO: 7) |
| orf7 spacer for cloning in pCas9 | 5'-AAAACGAGAAAATAGGAGAATTT AT-3' (SEQ ID NO: 8) |
| orf7 forward sgRNA template assembly | 5'-TAATACGACTCACTATAGTAAAT TCTCCTATTTTCTC-3' (SEQ ID NO: 9) |
| orf7 reverse sgRNA template assembly | 5'-TTCTAGCTCTAAAACGAGAAAAT AGGAGAATTTA-3' (SEQ ID NO: 10) |

Construction of DNA donor template for homology-directed repair: To generate a single point mutation in orf7, a single-stranded donor template was designed as 150 oligodeoxynucleotides (ssODN) and purchased from Integrated DNA Technologies as PAGE purified long oligos (ultra oligo). This included a single nucleotide change (G to A) flanked by a left 75 nucleotides homology arm and a right 74 nucleotides homology arm; the ssODN sequence is listed in Table 3. The single nucleotide change was located within the PAM sequence preventing re-cutting of the edited region. To insert a complete exogenous gene, the generation of the donor template with the homologues recombination vector system were custom-made by VectorBuilder. The plasmids containing plasmid donor DNA (pDonor) were designed to comprise an insert gene flanked by a left 500 nucleotides homology arm and a right 561 nucleotides homology arm. The DNA sequence of the different insert genes encoding enhanced green fluorescent protein (eGFP), *Bacillus thuringiensis* crystal toxin (Cry3Aa), *Bacillus thuringiensis* cytolytic toxin (Cyt2Ca1) and *Galanthus nivalis* agglutinin (GNA3); respective reverse sequence of inserts (–R); and the homologous arms are listed in Table 3. Plasmids were prepared by using the QIAGEN Maxi Plasmid Kit (QIAGEN).

TABLE 3

| Donor DNA. Plasmid donor templates were designed to include the reverse sequence order (-R). | |
|---|---|
| orf7 ssODN | CAAGTAATTCCATTAAAACTTCCCTTGCTTGCTCAATACTTACACCCT GCTCAATAAATTCTCCTATTTTCTCTGACATTCGTGATAAGTTACATA AACGTATTAATTCAACAACTTCAGTACGATACTTAGTTAAATTATCA GTTTCTA (SEQ ID NO: 11) |
| pGFP | ATGGTGAGCAAGGGCGAGGAGCTGTTCACCGGGGTGGTGCCCATCCT GGTCGAGCTGGACGGCGACGTAAACGGCCACAAGTTCAGCGTGTCC GGCGAGGGCGAGGGCGATGCCACCTACGGCAAGCTGACCCTGAAGT TCATCTGCACCACCGGCAAGCTGCCCGTGCCCTGGCCCACCCTCGTG ACCACCCTGACCTACGGCGTGCAGTGCTTCAGCCGCTACCCCGACCA CATGAAGCAGCACGACTTCTTCAAGTCCGCCATGCCCGAAGGCTACG |

TABLE 3-continued

Donor DNA. Plasmid donor templates were designed to include the reverse sequence order (-R).

|  |  |
|---|---|
|  | TCCAGGAGCGCACCATCTTCTTCAAGGACGACGGCAACTACAAGACC<br>CGCGCCGAGGTGAAGTTCGAGGGCGACACCCTGGTGAACCGCATCG<br>AGCTGAAGGGCATCGACTTCAAGGAGGACGGCAACATCCTGGGGCA<br>CAAGCTGGAGTACAACTACAACAGCCACAACGTCTATATCATGGCCG<br>ACAAGCAGAAGAACGGCATCAAGGTGAACTTCAAGATCCGCCACAA<br>CATCGAGGACGGCAGCGTGCAGCTCGCCGACCACTACCAGCAGAAC<br>ACCCCCATCGGCGACGGCCCCGTGCTGCTGCCCGACAACCACTACCT<br>GAGCACCCAGTCCGCCCTGAGCAAAGACCCCAACGAGAAGCGCGAT<br>CACACATGGTCCTGCTGGAGTTCGTGACCGCCGCCGGGATCACTCTCGG<br>CATGGACGAGCTGTACAAGTAAAGCG (SEQ ID NO: 12) |
| pGFP-R | GCGAAATGAACATGTCGAGCAGGTACGGCTCTCACTAGGGCCGCCGC<br>CAGTGCTTGAGGTCGTCCTGGTACACTAGCGCGAAGAGCAACCCCAG<br>AAACGAGTCCCGCCTGACCCACGAGTCCATCACCAACAGCCCGTCGT<br>CGTGCCCCGGCAGCGGCTACCCCCACAAGACGACCATCACCAGCCGC<br>TCGACGTGCGACGGCAGGAGCTACAACACCGCCTAGAACTTCAAGTG<br>GAACTACGGCAAGAAGACGAACAGCCGGTACTATATCTGCAACACC<br>GACAACATCAACATGAGGTCGAACACGGGGTCCTACAACGGCAGGA<br>GGAACTTCAGCTACGGGAAGTCGAGCTACGCCAAGTGGTCCCACAGC<br>GGGAGCTTGAAGTGGAGCCGCGCCCAGAACATCAACGGCAGCAGGA<br>ACTTCTTCTACCACGCGAGGACCTGCATCGGAAGCCCGTACCGCCTG<br>AACTTCTTCAGCACGACGAAGTACACCAGCCCCATCGCCGACTTCGT<br>GACGTGCGGCATCCAGTCCCACCAGTGCTCCCACCCGGTCCCGTGCC<br>CGTCGAACGGCCACCACGTCTACTTGAAGTCCCAGTCGAACGGCATC<br>CACCGTAGCGGGAGCGGGAGCGGCCTGTGCGACTTGAACACCGGCA<br>AATGCAGCGGCAGGTCGAGCTGGTCCTACCCGTGGTGGGGCCACTTG<br>TCGAGGAGCGGGAACGAGTGGTA (SEQ ID NO: 13) |
| pCry3Aa | TTTGGTGGAGCGCTTGTTTCGTTTTATACAAACTTTTTAAATACTATTT<br>GGCCAAGTGAAGACCCGTGGAAGGCTTTTATGGAACAAGTAGAAGC<br>ATTGATGGATCAGAAAATAGCTGATTATGCAAAAAATAAAGCTCTTG<br>CAGAGTTACAGGGCCTTCAAAATAATGTCGAAGATTATGTGAGTGCA<br>TTGAGTTCATGGCAAAAAAATCCTGTGAGTTCACGAAATCCACATAG<br>CCAGGGGCGGATAAGAGAGCTGTTTTCTCAAGCAGAAAGTCATTTTC<br>GTAATTCAATGCCTTCGTTTGCAATTTCTGGATACGAGGTTCTATTTC<br>TAACAACATATGCACAAGCTGCCAACATACATTTATTTTTACTAAAA<br>GACGCTCAAATTTATGGAGAAGAATGGGGATACGAAAAAGAAGATA<br>TTGCTGAATTTTATAAAAGACAACTAAAACTTACGCAAGAATATACT<br>GACCATTGTGTCAAATGGTATAATGTTGGATTAGATAAATTAAGAGG<br>TTCATCTTATGAATCTTGGGTAAACTTTAACCGTTATCGCAGAGAGAT<br>GACATTAACAGTATTAGATTTAATTGCACTATTTCCATTGTATGATGT<br>TCGGCTATACCCAAAAGAAGTTAAAACCGAATTAACAAGAGACGTTT<br>TAACAGATCCAATTGTCGGAGTCAACAACCTTAGGGGCTATGGAACA<br>ACCTTCTCTAATATAGAAAATTATATTCGAAAACCACATCTATTTGAC<br>TATCTGCATAGAATTCAATTTCACACGCGGTTCCGACCAGGATACTA<br>TGGAAATGACTCTTTCAATTATTGGTCCGGTAATTATGTTTCAACTAG<br>ACCAAGCATAGGATCAAATGATATAATCACATCTCCATTCTATGGAA<br>ATAAATCCAGTGAACCTGTACAAAATTTAGAATTTAATGGAGAAAAA<br>GTCTATAGAGCCGTAGCAAATACAAATCTTGCGGTCTGGCCGTCCGC<br>TGTATATTCAGGTGTTACAAAAGTGGAATTTAGCCAATATAATGATC<br>AAACAGATGAAGCAAGTACACAAACGTACGACTCAAAAAGAAATGT<br>TGGCGCGGTCAGCTGGGATTCTATCGATCAATTGCCTCCAGAAACAA<br>CAGATGAACCTCCAGAAAAGGGATATAGCCATCAACTCAATTATGTA<br>ATGTGCTTTTTAATGCAGGGTAGTAGAGGAACAATCCCAGTGTTAAC<br>TTGGACACATAAAAGTGTAGACTTTTTTAACATGATTGATTCGAAAA<br>AAATTACACAACTTCCGTTAGTAAAGGCATATAAGTTACAATCTGGT<br>GCTTCCGTTGTCGCAGGTCCTAGGTTTACAGGAGGAGATATCATTCA<br>ATGCACAGAAAATGGAAGTGCGGCAACTATTTACGTTACACCGGATG<br>TGTCGTACTCTCAAAAACATCGAGCTAGAATTCATTATGCTTCTACAT<br>CTCAGATAACATTTACACTCAGTTTAGACGGGGCACCATTTAATCAA<br>TACTATTTCGATAAAACGATAAATAAAGGAGACACATTAACGTATAA<br>TTCATTTAATTTAGCAAGTTTCAGCACACCATTCGAATTATCGGGGAA<br>TAACTTACAAATAGGCGTCACAGGATTAAGTGCTGGAGATAAAGTTT<br>ATATAGACAAAATTGAATTTATTCCAGTGAATTAA (SEQ ID NO: 14) |
| pCry3Aa-R | AATTAAGTGACCTTATTTAAGTTAAAACAGATATATTTGAAATAGAG<br>GTCGTGAATTAGGACACTGCGGATAAACATTCAATAAGGGGCTATTA<br>AGCTTACCACACGACTTTGAACGATTTAATTTACTTAATATGCAATTA<br>CACAGAGGAAATAAATAGCAAAATAGCTTTATCATAACTAATTTACC<br>ACGGGGCAGATTTGACTCACATTTACAATAGACTCTACATCTTCGTAT<br>TACTTAAGATCGAGCTACAAAAACTCTCATGCTGTGTAGGCCACATT<br>GCATTTATCAACGGCGTGAAGGTAAAAGCACGTAACTTACTATAGA<br>GGAGGACATTTGGATCCTGGACGCTGTTGCCTTCGTGGTCTAACATT<br>GAATATACGGAAATGATTGCCTTCAACACATTAAAAAAAGCTTAGTT<br>AGTACAATTTTTTCAGATGTGAAAATACACAGGTTCAATTGTGACCC<br>TAACAAGGAGATGATGGGACGTAATTTTTCGTGTAATGTATTAACTC<br>AACTACCGATATAGGGAAAAGACCTCCAAGTAGACAACAAAGACCT |

TABLE 3-continued

Donor DNA. Plasmid donor templates were designed to include the reverse sequence order (-R).

|  |  |
|---|---|
|  | CCGTTAACTAGCTATCTTAGGGTCGACTGGCGCGGTTGTAAAGAAAA<br>ACTCAGCATGCAAACACATGAACGAAGTAGACAAACTAGTAATATA<br>ACCGATTTAAGGTGAAAACATTGTGGACTTATATGTCGCCTGCCGGT<br>CTGGCGTTCTAAACATAAACGATGCCGAGATATCTGAAAAAGAGGTA<br>ATTTAAGATTTAAAACATGTCCAAGTGACCTAAATAAAGGTATCTTA<br>CCTCTACACTAATATAGTAAACTAGGATACGAACCAGATCAACTTTG<br>TATTAATGGCCTGGTTATTAACTTTCTCAGTAAAGGTATCATAGGACC<br>AGCCTTGGCGCACACTTTAACTTAAGATACGTCTATCAGTTTATCTAC<br>ACCAAAAGCTTATATTAAAAGATATAATCTCTTCCAACAAGGTATCG<br>GGGATTCCAACAACTGAGGCTGTTAACCTAGACAATTTTGCAGAGAA<br>CAATTAAGCCAAAATTGAAGAAAACCCATATCGGCTTGTAGTATGTT<br>ACCTTTATCACGTTAATTTAGATTATGACAATTACAGTAGAGAGACG<br>CTATTGCCAATTTCAAATGGGTTCTAAGTATTCTACTTGGAGAATTAA<br>ATAGATTAGGTTGTAATATGGTAAACTGTGTTACCAGTCATATAAGA<br>ACGCATTCAAAATCAACAGAAAATATTTTAAGTCGTTATAGAAGAAA<br>AAGCATAGGGGTAAGAAGAGGTATTTAAACTCGCAGAAAATCATTTT<br>TATTTACATACAACCGTCGAACACGTATACAACAATCTTTATCTTGGA<br>GCATAGGTCTTTAACGTTTGCTTCCGTAACTTAATGCTTTTACTGAAA<br>GACGAACTCTTTTGTCGAGAGAATAGGCGGGGACCGATACACCTAAA<br>GCACTTGAGTGTCCTAAAAAAACGGTACTTGAGTTACGTGAGTGTAT<br>TAGAAGCTGTAATAAAACTTCCGGGACATTGAGACGTTCTCGAAATA<br>AAAAACGTATTAGTCGATAAAAGACTAGGTAGTTACGAAGATGAAC<br>AAGGTATTTTCGGAAGGTGCCCAGAAGTGAACCGGTTTATCATAAAT<br>TTTTCAAACATATTTTGCTTTGTTCGCGAGGTGGTTT (SEQ ID NO: 15) |
| pCyt2Ca1 | ATGTTCTTCAACCGCGTTATCACCTTGACCGTTCCAAGCAGCGATGTC<br>GTTAACTACAGCGAAATCTACCAGGTCGCTCCACAGTATGTTAACCA<br>GGCTTTGACCTTGGCTAAGTACTTCCAGGGAGCTATCGATGGTAGCA<br>CCTTGAGATTCGATTTCGAGAAGGCTTTGCAGATTGCTAACGATATTC<br>CACAGGCAGCCGTGGTCAACACCTTGAATCAGACTGTCCAGCAAGGT<br>ACTGTCCAAGTCAGCGTGATGATCGACAAGATTGTCGACATTATGAA<br>GAATGTGTTGAGCATTGTCATTGATAACAAAAAGTTCTGGGATCAGG<br>TGACTGCTGCTATTACTAATACCTTCACCAACTTGAACAGCCAAGAA<br>AGCGAAAGATGGATTTTCTACTACAAGGAAGATGCTCACAAGACTAG<br>CTACTATTACAATATCTTGTTTGCTATTCAGGATGAGGAAACTGGTGG<br>CGTTATGGCCACCTTGCCAATCGCCTTTGATATTAGCGTTGATATTGA<br>AAAGGAAAAGGTTTTGTTTGTTACTATCAAGGATACTGAGAATTACG<br>CTGTTACCGTGAAAGCTATCAACGTCGTTCAGGCTTTGCAAAGCAGC<br>AGAGATAGCAAAGTTGTGGATGCTTTTAAAAGCCCAAGACACTTGCC<br>AAGAAAAAGACACAAAATCTGCAGCAACAGCTAA (SEQ ID NO: 16) |
| pCyt2Ca1-R | AATCGACAACGACGTCTAAAACACAGAAAAAGAACCGTTCACAGAA<br>CCCGAAAATTTTCGTAGGTGTTGAAACGATAGAGACGACGAAACGTT<br>TCGGACTTGCTGCAACTATCGAAAGTGCCATTGTCGCATTAAGAGTC<br>ATAGGAACTATCATTGTTTGTTTGGAAAAGGAAAAGTTATAGTTGC<br>GATTATAGTTTCCGCTAACCGTTCCACCGGTATTGCGGTGGTCAAAG<br>GAGTAGGACTTATCGTTTGTTCTATAACATTATCATCGATCAGAACAC<br>TCGTAGAAGGAACATCATCTTTTAGGTAGAAAGCGAAAGAACCGAC<br>AAGTTCAACCACTTCCATAATCATTATCGTCGTCAGTGGACTAGGGT<br>CTTGAAAAACAATAGTTACTGTTACGAGTTGTGTAAGAAGTATTACA<br>GCTGTTAGAACAGCTAGTAGTGCGACTGAACCTGTCATGGAACGACC<br>TGTCAGACTAAGTTCCACAACTGGTGCCGACGGACACCTTATAGCAA<br>TCGTTAGACGTTTCGGAAGAGCTTTAGCTTAGAGTTCCACGATGGTA<br>GCTATCGAGGGACCTTCATGAATCGGTTCCAGTTTCGGACCAATTGT<br>ATGACACCTCGCTGGACCATCTAAAGCGACATCAATTGCTGTAGCGA<br>CGAACCTTGCCAGTTCCACTATTGCGCCAACTTCTTGTA (SEQ ID NO: 17) |
| pGNA3 | ATGGCTAAGGCAAGTCTCCTCATTTTGGCTACCATCTTTCTTGGAGTC<br>ATCACACCAGCTTGCCTGAGTGAAAATATTCTGTACTCCGGTGAGAC<br>TCTCCCTACAGGGGGATTTCTCACCTCTGGCAGTTTTGTTTTTATCAT<br>GCAAGAGGACTGCAACCTGGTCTTGTACAACGTCGACAAGCCCATCT<br>GGGCAACTAACACAGGCGGCCTCTCCAGTGACTGCTCCCTCAGCATG<br>CAGACCGATGGGAACCTCGTTGTGTACACCCCATCGGACAAACCGAT<br>TTGGGCAAGCGACACTGACGGTCAGAATGGGAATTACGTGTGCATCC<br>ATCAAAAGGATCGGAACGTTGTGATCTACGGAACTAATCGTTGGGCT<br>ACTGGAACTCACACCGGCGCTGTAGGAATTCCTGCATCACCGCCCTC<br>GGAGAAATATCCTACTGCTGGAATGATAAAGCTTGTGACGGCAAAGT<br>AA (SEQ ID NO: 18) |
| pGNA3-R | AATGAAACGGCAGTGTTCGAAATAGTAAGGTCGTCATCCTATAAAGA<br>GGCTCCCGCCACTACGTCCTTAAGGATGTCGCGGCCACACTCAAGGT<br>CATCGGGTTGCTAATCAAGGCATCTAGTGTTGCAAGGCTAGGAAAAC<br>TACCTACGTGTGCATTAAGGGTAAGACTGGCAGTCACAGCGAACGGG<br>TTTAGCCAAACAGGCTACCCCACATGTGTTGCTCCAAGGGTAGCCAG<br>ACGTACGACTCCCTCGTCAGTGACCTCTCCGGCGGACACAATCAACG<br>GGTCTACCCGAACAGCTGCAACATGTTCTGGTCCAACGTCAGGAGAA |

TABLE 3-continued

Donor DNA. Plasmid donor templates were designed to include the reverse sequence order (-R).

| | |
|---|---|
| | CGTACTATTTTTGTTTTGACGGTCTCCACTCTTTAGGGGGACATCCCT<br>CTCAGAGTGGCCTCATGTCTTATAAAAGTGAGTCCGTTCGACCACAC<br>TACTGAGGTTCTTTCTACCATCGGTTTTACTCCTCTGAACGGAATCGG<br>TA (SEQ ID NO: 19) |
| Plasmid left homologous arm | ACTCCTTTACTATTTTCCTTTGCGTTTACATCGCTTGCTATTACACCTA<br>TCGCTGTTTGTGTACCATCTGTGGCAGTTGGATTTAAAGCTTTAATTA<br>AATTATCTTTAGTATCATAACCAACTACTGTTCCTAGCTTCAGATTTT<br>GTCCCTTTGCTACCGTTATTTGGTCTCTTGAATATAAACTTGATGCCT<br>CATACTTTAATAGGTCACCTAGATTATTTTGTTCGGTTATACATGTCA<br>TATTTTCTTTTCTCCTTTTTTCCTTTAGTTTTACCGCCATGTTTGTAGTT<br>ATTGTATGCGGCGGTTATAAAAAAACTTAAATACTTGATTGTGCTCT<br>AGCTTTTGCTACTTGCATCATCAAATCTTCTCCTGAATTCTGTGGTAT<br>TGCACTCAGTATCTCTGTCTTCTTCGTTCTCTCTGCAAGTAATTCCATT<br>AAAACTTCCCTTGCTTGCTCAATACTTACACCCTGCTCAATAAATTCT<br>CCTATTTTCTCTGACAT (SEQ ID NO: 20) |
| Plasmid right homologous arm | TCGTGATAAGTTACATAAACGTATTAATTCAACAACTTCAGTACGAT<br>ACTTAGTTAAATTATCAGTTTCTAGGTCACTTGTAGTTTGTTTATTCAT<br>AGTATTTTCTCCTTTGTTAATAAATTCAAAAAATGTTGTAACTCCATC<br>TGCAAGACCTATTTCTACTGCTTTCTCACCAAAATATAGACCTGCTTC<br>AGTATTTTTATTGCTTGTACAGAAAGTCCTCTGTTTCGTGCTATAAG<br>TTCAGTCAGAATTTCATATAAGCGATTTACTTCCTCCTCTAAACTTTT<br>TAAGCTTTCTAAACTTATAGGCTCATGTGGATTTAAATCATTCTTTCT<br>CTTGCCTGCAAAAATAGTTGTGTATTTTATTCCTTGCTTTTCATCAAA<br>CCTACTTTGATCTATATGACTTGCTATTACTCCTATACTGCCAACACC<br>AAAAGTTCTGCTCACAAATACCTTTTCAGCACTTGAAGCTATAGCAT<br>ATGCAGCAGAGTACGCATCATCATTTGCTATTGCCACAATTCTCTTTT<br>TTGCTCTTGATTCGTAAATAAAATCAGCCAAGTC (SEQ ID NO: 21) | wDi transformation: Extraction of wDi from S2+wDi cells and electroporation of wDi cells were conducted as described in Example 1. Each electroporation sample contained 500,000-850,000 wDi cells. Isolated wDi cells were transformed with (1) 2 µg of pCas9+sgRNA and 1 µL of 10 µM ssODN (plasmid based system) or (2) 1 µg of GeneArt™ Platinum™ Cas9 nuclease, 200 ng of sgRNAs and either 1 µL of 1 µM ssODN or 500 ng of pDonor DNA (protein based system).

PCR analysis: DNA extractions for both cell culture and D. citri samples were conducted using DNeasy Blood and Tissue kit (QIAGEN). DNA concentrations were quantified by spectrophotometry (Nanodrop 2000; Thermo Fisher Scientific). DNA samples were diluted to 10 ng/µL for subsequent PCR analysis. GoTaq Colorless Master Mix (Promega) and T100 thermal cycle (Bio-Rad) were used for the PCR analysis. All samples were screened for wDi presence using the wsp gene (*Wolbachia* outer surface protein). Only samples that were positive for wsp were further analyzed to detect genome editing. The pair of primers for amplifying the targeted region or insert gene were designed using Primer3 v 0.40 software (Untergrasser et al., 2012) and listed in Table 3. The amplicon sequences were verified by Sanger DNA sequencing (Genewiz).

TABLE 3

PCR primers used in this study.

| Target Gene | Primer sequence (5'-3') | SEQ ID NO: |
|---|---|---|
| Wsp-forward | AGG GCT TTA CTC AAA ATT GG | 22 |
| Wsp-reverse | CAC CAA CGG TAT GGA GTG ATA GG | 23 |
| GFP-forward | GGT GAA CTT CAA GAT CCG CC | 24 |
| GFP-reverse | CTT GTA CAG CTC GTC CAT GC | 25 |
| GFP-R-forward | CAG GTA CGG CTC TCA CTA GG | 26 |
| GFP-R-reverse | TAC CGG CTG TTC GTC TTC TT | 27 |
| Cry3Aa-forward | TTG TCG CAG GTC CTA GGT TT | 28 |
| Cry3Aa-reverse | AAT GGT GCC CCG TCT AAA CT | 29 |
| Cry3Aa-R-forward | GTG TAG GCC ACA TTG CAT TTA TC | 30 |
| Cry3Aa-R-reverse | CGT CCC ATC ATC TCC TTG TTA G | 31 |
| Cyt2Ca1-forward | GAT CAG GTG ACT GCT GCT ATT A | 32 |
| Cyt2Ca1-reverse | CTT TGC TAT CTC TGC TGC TTT G | 33 |
| Cyt2Ca1-R-forward | GAA AGC GAA AGA ACC GAC AAG | 34 |
| Cyt2Ca1-R-reverse | GCT ACC ATC GTG GAA CTC TAA G | 35 |
| GNA3-forward | GGC TAC CAT CTT TCT TGG AGT C | 36 |
| GNA3-reverse | CTT TGC CGT CAC AAG CTT TAT C | 37 |
| GNA3-R-forward | ACA CTC AAG GTC ATC GGG TT | 38 |
| GNA3-R-reverse | CCA GAA CAT GTT GCA GCT GT | 39 |

FACS analysis: wDi cells were collected two days after transformation, then washed and resuspended in phosphate buffer saline (PBS). Fluorescence-activated cell sorting (FACS) analysis of GFP transformed wDi cells were performed using a BD FACSAria II flow cytometer (BD Biosciences) at the Cytometry Core Facility in University of Florida Interdisciplinary Center for Biotechnology Research. Electroporated samples of wDi without DNA (negative control) and wDi with fluorescein-labeled dsRNA oligo (BLOCK-iT™ Fluorescent Oligo) (positive control) were used to set gating parameters.

Nymph microinjections: Two electroporated wDi samples were combined and resuspended in PBS, followed by microinjection into D. citri nymphs (3rd-4th instars) at their ventral side of the first abdominal segment or dorsal side of the mesothorax. The range of injection pressure used was 12-15 psi, and approximately 0.2 µl of wDi cell suspension was injected per nymph. After injection, nymphs were placed on *Citrus macrophylla* plants to further develop into adults. Psyllids were collected after detecting eggs on the host plants and screened for exogenous gene insert from the transformed wDi.

Imaging: Transformed wDi cells were sorted, and the GFP-positive population (wDi+GFP) was processed for in vivo imaging. wDi+GFP cells were suspended in PBS, mounted on a cover glass and placed on a microscope slide. Each slide was imaged in three different locations to screen for GFP-positive cells. wDi-control cells were electroporated with no DNA while two independent electroporated samples with CRISPR/Cas9 components are shown in FIG. 11D. Fluorescent images were acquired using an Olympus BX61 fluorescent compound microscope. S2+wDi+GFP-R sorted cells were stained with 17 μg/μl Hoechst 33342 (Thermo Fisher Scientific). Cells were allowed to settle on CELLview™ cell culture dishes (sterile glass bottom) and analyzed with a Leica SP5 inverted confocal microscope (FIG. 11E). For the microinjections on *D. citri*, the transformed wDi+GFP-R were stained with Hoechst 33342 before they were microinjected. Due to autofluorescence in the nymph, cells that were positive for both GFP and Hoechst 33342 signal were indicated as transformed wDi+GFP-R (FIG. 13A, red arrows). Low-melt agarose was used for mounting the injected nymphs. Nymphs were images 1-2 h post-injection. In vivo images were taken using a Leica SP8 upright confocal microscope.

Results wDi Culture Undergo Gene Editing Via CRISPR/Cas9-Mediated Homology-Directed Repair.

A single nucleotide change in wDi prophage was produced in order to determine whether wDi cells were responsive to CRISPR/Cas9-mediated homology-directed repair (HDR) gene editing. The targeted location for bioengineering wDi was the minor capsid gene (orf7) of the *Wolbachia*-associated phage (WO). CRISPR sgRNA was designed within orf7 of wDi and the single-stranded DNA oligonucleotide (ssODN) donor, including the two flanking homology arms and the G to A mutation (sequences are shown in FIG. 8A and Table 2). The schematic outline to transform wDi with the CRISPR/Cas9-plasmid or -protein based system strategy is shown in FIG. 8B. This strategy made use of pCas9 plasmid, the commercially available Cas9 endonuclease and the synthetic, mutation-inducing oligonucleotide (donor DNA).

DNA was isolated from cells transfected with the different gene editing strategies (plasmid or protein) in order to analyze the sequence change in wDi after CRISPR/Cas9-mediated HDR (FIG. 9). For the plasmid based system, wDi cells were electroporated with either no CRISPR/Cas9 components (control), pCas9 (without the guide sequence), pCas9+sgRNA (without donor DNA), or pCas9+sgRNA+ssODN (FIG. 9A). For the protein based system, wDi cells were electroporated with either no CRISPR/Cas9 components (control), Cas9:sgRNA (without donor DNA) or Cas9:sgRNA+ssODN (FIG. 9B). In both the plasmid and protein based systems, the detection of single base gene editing occurred; however, as expected, not all cells within an electroporated sample were genetically transformed resulting in a heterogenous population.

In a separate biological sample, three technical replicates from the sample wDi population were used to analyze the variability of each system. wDi cells that were transfected with pCas9+sgRNA+ssODN resulted in one of three samples with the point mutation (data not shown); whereas, wDi cells transfected with Cas9:sgRNA+ssODN resulted in three of three samples with the point mutation (FIG. 9C). The protein based strategy was used for gene insert experiments.

Knock-in of eGFP in wDi: The *Wolbachia* were isolated from host cells and transfected with CRISPR-Cas9 components plus circular pGFP or pGFP-R to integrate an exogenous gene via CRISPR/Cas9-mediated HDR in wDi. S2 cells were infected with two days post-transformed wDi cells (S2+wDi) (FIG. 10). Genomic DNA of transfected cells, wDi and S2+wDi, were extracted and analyzed by PCR (FIGS. 11A & 11B). GFP insertion was confirmed in both wDi and S2+wDi cell cultures by the occurrence of the PCR product in transfected cells and absent in the negative control samples (no pDonor). After two days of transfection, wDi+GFP and wDi+GFP-R cells were subsequently enriched by fluorescence-activated cell sorting (FACS) (FIG. 11C). Cells transformed with pGFP or pGFP-R had 4.8% and 6.2% GFP-positive wDi cells, respectively. Both directions of the gene insert were able to produce GFP; however, the GFP intensity signal was higher with the reverse sequence. Successful production of GFP was also demonstrated by in vivo imaging, observing a heterogenous population in terms of signal intensity (FIG. 11D, red arrows). In addition, by in vivo imaging of S2+wDi+GFP-R cells, the production of GFP by wDi cells in host cells (S2) was visible (FIG. 11E). These results demonstrated the ability for CRISPR/Cas9-assisted HDR to knock-in a transgenes, GFP, in wDi; in addition, the transformed wDi cells remain viable in host cells.

Generation of wDi+toxin cell lines: Next, several toxins were introduced into wDi which are promising agents against insect pests. Using the same strategy as before, *Bacillus thuringiensis* crystal toxin Cry3Aa (1686 bp), *Bacillus thuringiensis* cytolytic toxin Cyt2Ca1 (696 bp) or *Galanthus nivalis* agglutinin GNA3 (474 bp) were introduced within the pDonor (FIG. 12A). All toxin genes were introduced into the pDonor with the forward and reverse order. PCR assays verified incorporation of toxin genes in S2+wDi+toxin cells (FIG. 12B-12G). PCR amplicons were sequenced to confirm their identity to desired transgene. These results demonstrated the successful integration of the donor DNA and that integration described herein is applicable across genes of variant sizes.

Paratransgenic *D. citri* with transformed wDi+: Paratransgenesis involves genetic manipulation of symbiotic bacteria commonly found in pathogen-transmitting vectors to export anti-pathogen "effector" molecules into the host vector. Paratransgenic strategy to control insect-borne diseases depends on the ability to genetically modify microorganisms from an insect. The ability for the transformed wDi+ to establish and vertically transmit themselves in *D. citri* was tested. To bypass the midgut barrier, *D. citri* nymphs were microinjected with transformed wDi+ to increase the changes of vertical transmission. Early dispersal of wDi+GFP-R in injected nymphs were detected (FIG. 6A) by in vivo imaging. By 1-2 h post-injection, transformed cells (FIG. 13A, red arrows) were visualized near or distal from the injection location (FIG. 13A, yellow arrows). Due to concerns with toxic effects of GFP in the insect, further microinjections were conducted with wDi+Cry3Aa or wDi+Cry3Aa-R because there are no known reports of Cry3Aa being toxic to *D. citri*. No live *D. citri* adults were able to collect from plants that had nymphs injected with wDi+Cry3Aa. However, nymphs injected with wDi+Cry3Aa-R did survive to adulthood. No wDi+Cry3Aa-R was detected by PCR in the parental generation (data not shown). By the F1 generation, there were five wDi+Cry3Aa-R positive *D.*

*citri* out of 19 individual that were tested (26.3%) (FIG. 13B). The number of positive wDi+Cry3Aa-R *D. citri* increased to 21 out of 24 that were tested of the F3 generation (87.5%) (FIG. 13C). Thus, the percent of offspring infected with the transformed wDi+ was higher in F3 compared to F1 generation.

Genetically engineered *Wolbachia* containing the holin-repressor gene also were generated using the methods described herein. Paratransgenic transformation of *D. citri* with the holin-repressor gene eliminated CLas plant infection, as well as acquisition, suggesting that the paratransgenic *Wolbachia* is useful tool for disrupting of insect-transmitted pathogens. Additional replicates were collected which confirmed successful inhibition of CLas in *D. citri* transformed with *Wolbachia* containing holin-repressor gene (wDi$^{-HRP}$). CLas was not detected in susceptible citrus plants following exposure to *D. citri* with wDi$^{-HRP}$ following acquisition feeding infected plants. This confirms that CLas transmission was disrupted with paratransgenic *Wolbachia*.

The foregoing Example describes the successful confirmation of paratransgenesis using the endosymbiont, *Wolbachia*. Transformed *Wolbachia* able to express an exogenous gene were established in the insect host (*D. citri*) and were vertically transmitted from mother to offspring.

Example 3—Additional Paratransgenesis Examples

*Wolbachia* is present in 40% of insect species, rendering it a promiscuous insect symbiont. Given the cosmopolitan nature of the symbiont, it is likely that the *Wolbachia* driver system developed can be incorporated across a wide range of insect species for paratransgenic transformation. The implications of this are particularly important for the potential use of paratransgenic strategies to control insect-borne diseases.

The *Wolbachia* transformation system and methods described in Example 2 were used to successfully paratransgenic transform insects in three different orders: Hemiptera, Diptera, and Lepidoptera (data not shown).

This Example demonstrates that paratrangenesis can be used widely across a large range of insect species, without the need to develop a unique endosymbiont cell line for every insect target.

The foregoing Examples demonstrate that genetically-transformed *Wolbachia* is a flexible tool for, e.g., arthropod control, and facilitates the exogenous expression of a number of foreign genes, including insecticidal toxins, Gfp proteins, and CLas-associated genes. Significantly, the use of the genetically-transformed *Wolbachia* to paratransgenically engineer *D. citri* that do not transmit CLas was demonstrated. This finding is a significant demonstration that paratransgenesis can be used to reduce the spread of vector-borne pathogens, which may be extended to other pathosystems, such as mosquito-borne arboviruses, *Plasmodium*, etc.

Example 4—Insecticidal Activity

Honeydew assays. Honeydew will be collected from paratransgenic *D. citri* produced according to the methods described in Example 2 to evaluate production of Cry toxins by *D. citri*. Honeydew produced during insect feeding will be collected on the underside of an inverted Petri dish placed under a leaf disc. A glass pipette will be used to collect honeydew for subsequent detection of Cry toxins via Western blotting. In the event no toxins are detected, whole insects will be ground, centrifuged, and the supernatant collected for Cry toxin detection. Extracted honeydew will be used in subsequent insecticidal bioassays.

Insecticidal activity bioassays. Honeydew (or whole-body extracts) produced by paratransgenic *D. citri* will be used to assess Cry activity against Coleopteran larvae. *Diaprepes abbreviatus*, also pests of citrus, are maintained in colony in a insect rearing facility at the University of Florida Citrus Research and Education Center. Honeydew extracts from paratransgenic *D. citri* will be incorporated into artificial diet media in a 0.5 ul PCR tube. Neonate *D. abbreviatus* will be placed in tubes. Tubes will be inverted and stored at 27° C. for 2 weeks. Mortality will be recorded by inspecting larvae under a dissecting microscope. Mortality of larvae in response to paratransgenically-derived Cry toxin will be compared to mortality of beetles in response to optimum doses of exogenous Cry toxins incorporated in the artificial diet.

REFERENCES

Arora A K, Douglas A E (2017) Hype or opportunity? Using microbial symbionts in novel strategies for insect control. J Insect Physiol 103: 10-17.

Badawi M., Giraud I., Vevre F., Greve P., Cordaux R. (2014) Signs of Neutralization in a Redundant Gene Involved in Homologous Recombination in *Wolbachia* Endosymbionts. Genome Biol. Evol. 6(10):2654-2664.

Baum B, Cherbas L (2008) *Drosophila* cell lines as model systems and as an experimental tool. In Methods in Molecular Biology, Edited by: Dahmann C. Dresden, Germany: Max Planck Institute of Molecular Cell Biology and Genetics. p. 391-424.

Buster D W, Nye J, Klebba J E, Rogers G C (2010) Preparation of *Drosophila* S2 cells for Light Microscopy. J Vis Exp 40: e1982, doi: 10.3791/1982

Chu C C, Gill T A, Hoffmann M, Pelz-Stelinski K S (2016) Inter-population variability of endosymbiont densities in the Asian citrus psyllid (*Diaphorina citri* Kuwayama). Microb Ecol 71: 999-1007

Dobson S L, Rattanadechakul W. (2001) A noval technique for removing *Wolbachia* infection from *Aedes albopictus* (Diptera: Culicidae) J Med Entomolo 38:844-849.

Dossi F C A, da Silva E P, Consoli F L. (2014). Population dynamics and growth rates of endosymbionts during *Diaphorina citri* (Hemiptera: Liviidae) ontogeny. Microb Ecol 68:881. doi: 10.1007/s00248-014-0463-9.

Eleftherianos I, Atri J, Accetta J Castillo J C (2013) Endosymbiotic bacteria in insects: Guardians of the immune system? Front Physiol 4: 1-10.

Gamston C, Rasgon J. (2007) Maintaining *Wolbachia* in Cell-free Medium. J Vis Exp 5: e223, doi: 10.3791/223.

Hancock P A, Sinkins S P, Godfray H C (2011) Strategies for introducing *Wolbachia* to reduce transmission of mosquito-borne diseases. PLos Negl Trop Dis 5: e1024.

Hughes G L, Koga R, Xue P, Fukatsu T, Rasgon J L (2011) *Wolbachia* infections are virulent and inhibit the human malaria parasite *Plasmodium falciparum* in *Anopheles gambiase*. PLoS Pathog 7: 1002043. doi: http://dx.doi.org/10.1371/journal.ppat.1002043.

Jiang W, Bikard D, Cox D, Zhang F, Marraffini L A (2013) RNA-guided editing of bacterial genomes using CRISPR-Cas system. Nat Biotechnol 31:233-239.

Jiang Y, Chen B, Duan C, Sun B, Yang J, Yang S (2015) Multigene editing in the *Escherichia coli* genome via the CRISPR-Cas9 System. App Environ Microbial 81: 2506-2515.

Kambris Z, Cook P E, Phuc H K, Sinkins S P (2009) Immune activation by life-shortening *Wolbachia* and reduced filarial competence in mosquitoes. Science 326: 1374-136.

Moreira L A, Iturbe-Ormaetxe I, Jeffery J A, Lu G, Pyke A T, Hedges L M, et al. (2009) A *Wolbachia* symbiont in *Aedes aegypti* limits infection with dengue, Chikungunya, and *Plasmodium*. Cell 139: 1268-1278.

O'Neill S L, Pettigrew M M, Sinkins S P, Braig H R, Andreadis T G, Tesh R B. (1997) In vitro cultivation of *Wolbachia pipientis* in an *Aedes albopictus* cell line. Insect Mol Biol 6:33-39.

Rachek L I, Tucker A M, Winkler H H, Wood D O (1998) Transformation of *Rickettsia prowazekii* to rifampin resistance. J Bacteriol 180: 2118-2124.

Ragson J L, Gamston C E, Ren X (2006) Survival of *Wolbachia pipientis* in Cell-Free medium. Appl Environ Microbiol 72: 6934-6937.

Sambrook J, Russell D W (2001) Molecular cloning: A laboratory manual. Volume 1. Cold Spring Harbor (New York): Cold Spring Harbor Laboratory Press. 680p.

Stevens L, Giordano R, Fialho R F (2001) Male-killing, nematode infections, bacteriophage infection, and virulence of cytoplasmic bacteria in the genus *Wolbachia*. Annu Rev Entomol 32: 519-545.

Stouthamer R, Breeuwer J A, Hurst G D (1999) *Wolbachia pipientis*: Microbial manipulator of arthropod reproduction. Annu Rev Entomol 53: 71-102.

Texeira L, Ferreira A, Ashburner M (2008) The bacterial symbiont *Wolbachia* induces resistance to RNA viral infections in *Drosophila melanogaster*. PLos Biol. 6:e2. Doi: 10.1371/journal.pbio.1000002.

Untergrasser A., Cutcutache I., Koressaar T., Ye J., Faircloth B C., Remm M., Rozen S G. (2012) Primer3—New Capabilities and Interfaces. Nucleic Acids Res. 40:e115-e115.

Werren J (2007) Biology of *Wolbachia*. Annu Rev Entomol 42: 587-609.

Werren J H, Baldo L, Clark M E (2008) *Wolbachia*: Master manipulators of invertebrate biology. Nat Rev Microbiol 6: 741-751.

Yen J H, Barr A R (1973) The etiological agent of cytoplasmic oncompatibility in *Culex pipiens*. J Invertebr Pathol. 22: 242-250.

Zug R, Hammerstain P (212) Still a host of hosts for *Wolbachia*: Analysis of recent data suggests that 40% of terrestrial arthropod species are infected. PLos ONE 7: 0038544. Doi: http://dx.doi.org/10.1371/journal-.pone.0038544.

What is claimed is:

1. A method comprising
   (a) introducing into a *Wolbachia* bacterium a (i) nucleic acid encoding a Clustered Regularly Interspaced Short Palindromic Repeats (CRISPR)-associated (Cas)9 endonuclease, (ii) nucleic acid encoding a donor template toxin sequence, and (iii) a guide RNA selected from the group consisting of SEQ ID NOs 7, 8, 9, and 10; thereby producing a genetically transformed bacterium; and
   (b) introducing the genetically transformed bacterium into an arthropod.

2. The method of claim 1, wherein the method includes isolating the bacterium from an arthropod host before step (a).

3. The method of claim 1, wherein the arthropod is selected from the group consisting of an insect, an arachnid and a crustacean.

4. The method of claim 3, wherein the insect is selected from the group consisting of an Asian citrus psyllid (*Diaphorina citri*), Yellow fever mosquito (*Aedes aegypti*), Potato psyllid (*Bactericerca cockerelli*), German cockroach (*Blatella germanica*, Beg Bed bug (*Cimex lectularius*), fruit fly (*Drosophila melanogaster*), house cricket (*Acheta domesticus*), American grasshopper (*Schistocerca Americana*), tobacco hornworm (*Manduca sexta*) and a red flour beetle (*Tribolium castaneum*).

5. The method of claim 1, wherein the toxin is selected from the group consisting of *Bacillus thuringiensis* crystal toxin (Cry3Aa), *Bacillus thuringiensis* cytolytic toxin (Cyt2Ca1) and *Galanthus nivalis* agglutinin (GNA3).

6. The method of claim 2, further comprising the step of culturing the bacterium in a *Drosophila melanogaster* cell before step (a).

7. The method of claim 6, wherein the *Drosophila melanogaster* cell is Schneider 2 (S2) cell.

8. The method of claim 7, wherein the S2 cell is cultured in Schneider medium.

9. A method comprising
   (a) introducing into a *Wolbachia* bacterium a (i) nucleic acid encoding a Clustered Regularly Interspaced Short Palindromic Repeats (CRISPR)-associated (Cas)9 endonuclease, (ii) nucleic acid encoding a donor template toxin sequence, and (iii) a guide RNA selected from the group consisting of SEQ ID NOs 7, 8, 9, and 10; thereby producing a genetically transformed bacterium; and
   (b) introducing the genetically transformed bacterium into an Asian citrus psyllid (*Diaphorina citri*).

10. The method of claim 9, wherein the toxin is *Bacillus thuringiensis* crystal toxin (Cry3Aa).

* * * * *

```
SEQUENCE LISTING

<160> NUMBER OF SEQ ID NOS: 41

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
agggctttac tcaaaattgg                                              20

<210> SEQ ID NO 2
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 2
caccaacggt atggagtgat agg                                          23

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3
acgagccaga gaagcaagag                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 4
```

```
tacgtcgcac accttcaaaa                                               20

<210> SEQ ID NO 5
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 5
gcagtcggat accttcctat tc                                            22

<210> SEQ ID NO 6
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 6
tccctgatgg tcgtcatcta                                               20

<210> SEQ ID NO 7
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 7
aaacataaat tctcctattt tctcg                                         25

<210> SEQ ID NO 8
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 8
aaaacgagaa aataggagaa tttat                                         25

<210> SEQ ID NO 9
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 9
taatacgact cactatagta aattctccta ttttctc                            37

<210> SEQ ID NO 10
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 10
ttctagctct aaaacgagaa aataggagaa ttta                               34

<210> SEQ ID NO 11
<211> LENGTH: 150
<212> TYPE: DNA
```

<213> ORGANISM: Artificial Sequence
<220> FEATURE:
<223> OTHER INFORMATION: Synthetic Polynucleotide

<400> SEQUENCE: 11

```
caagtaattc cattaaaact tcccttgctt gctcaatact tacaccctgc tcaataaatt      60
ctcctatttt ctctgacatt cgtgataagt tacataaacg tattaattca acaacttcag     120
tacgatactt agttaaatta tcagtttcta                                      150
```

<210> SEQ ID NO 12
<211> LENGTH: 724
<212> TYPE: PRT
<213> ORGANISM: Artificial Sequence
<220> FEATURE:
<223> OTHER INFORMATION: Synthetic Polynucleotide

<400> SEQUENCE: 12

```
Ala Thr Gly Gly Thr Gly Ala Gly Cys Ala Ala Gly Gly Cys Gly
1               5                   10                  15

Ala Gly Gly Ala Gly Cys Thr Gly Thr Cys Ala Cys Gly Gly
            20                  25                  30

Gly Gly Thr Gly Gly Thr Gly Cys Cys Ala Thr Cys Cys Thr Gly
            35                  40                  45

Gly Thr Cys Gly Ala Gly Cys Thr Gly Gly Ala Cys Gly Gly Cys Gly
        50                  55                  60

Ala Cys Gly Thr Ala Ala Cys Gly Gly Cys Cys Ala Cys Ala Ala
65                  70                  75                  80

Gly Thr Thr Cys Ala Gly Cys Gly Thr Gly Thr Cys Cys Gly Gly Cys
            85                  90                  95

Gly Ala Gly Gly Gly Cys Gly Ala Gly Gly Gly Cys Gly Ala Thr Gly
            100                 105                 110

Cys Cys Ala Cys Cys Thr Ala Cys Gly Gly Cys Ala Ala Gly Cys Thr
            115                 120                 125

Gly Ala Cys Cys Cys Thr Gly Ala Ala Gly Thr Thr Cys Ala Thr Cys
            130                 135                 140

Thr Gly Cys Ala Cys Cys Ala Cys Cys Gly Gly Cys Ala Ala Gly Cys
145                 150                 155                 160

Thr Gly Cys Cys Cys Gly Thr Gly Cys Cys Thr Gly Gly Cys Cys
                165                 170                 175

Cys Ala Cys Cys Cys Thr Cys Gly Thr Gly Ala Cys Cys Ala Cys Cys
            180                 185                 190

Cys Thr Gly Ala Cys Cys Thr Ala Cys Gly Gly Cys Gly Thr Gly Cys
            195                 200                 205

Ala Gly Thr Gly Cys Thr Thr Cys Ala Gly Cys Cys Gly Cys Thr Ala
            210                 215                 220

Cys Cys Cys Cys Gly Ala Cys Cys Ala Cys Ala Thr Gly Ala Ala Gly
225                 230                 235                 240

Cys Ala Gly Cys Ala Cys Gly Ala Cys Thr Thr Cys Thr Thr Cys Ala
                245                 250                 255

Ala Gly Thr Cys Cys Gly Cys Cys Ala Thr Gly Cys Cys Gly Ala
            260                 265                 270

Ala Gly Gly Cys Thr Ala Cys Gly Thr Cys Cys Ala Gly Gly Ala Gly
            275                 280                 285

Cys Gly Cys Ala Cys Cys Ala Thr Cys Thr Thr Cys Thr Thr Cys Ala
            290                 295                 300
```

-continued

Ala Gly Gly Ala Cys Gly Ala Cys Gly Gly Cys Ala Ala Cys Thr Ala
305 310 315 320

Cys Ala Ala Gly Ala Cys Cys Cys Gly Cys Gly Cys Cys Gly Ala Gly
325 330 335

Gly Thr Gly Ala Ala Gly Thr Thr Cys Gly Ala Gly Gly Gly Cys Gly
340 345 350

Ala Cys Ala Cys Cys Cys Thr Gly Gly Thr Gly Ala Ala Cys Cys Gly
355 360 365

Cys Ala Thr Cys Gly Ala Gly Cys Thr Gly Ala Ala Gly Gly Gly Cys
370 375 380

Ala Thr Cys Gly Ala Cys Thr Thr Cys Ala Ala Gly Gly Ala Gly Gly
385 390 395 400

Ala Cys Gly Gly Cys Ala Ala Cys Ala Thr Cys Cys Thr Gly Gly Gly
405 410 415

Gly Cys Ala Cys Ala Ala Gly Cys Thr Gly Gly Ala Gly Thr Ala Cys
420 425 430

Ala Ala Cys Thr Ala Cys Ala Ala Cys Ala Gly Cys Cys Ala Cys Ala
435 440 445

Ala Cys Gly Thr Cys Thr Ala Thr Ala Thr Cys Ala Thr Gly Gly Cys
450 455 460

Cys Gly Ala Cys Ala Ala Gly Cys Ala Gly Ala Ala Gly Ala Ala Cys
465 470 475 480

Gly Gly Cys Ala Thr Cys Ala Ala Gly Gly Thr Gly Ala Ala Cys Thr
485 490 495

Thr Cys Ala Ala Gly Ala Thr Cys Cys Gly Cys Cys Ala Cys Ala Ala
500 505 510

Cys Ala Thr Cys Gly Ala Gly Gly Ala Cys Gly Gly Cys Ala Gly Cys
515 520 525

Gly Thr Gly Cys Ala Gly Cys Thr Cys Gly Cys Cys Gly Ala Cys Cys
530 535 540

Ala Cys Thr Ala Cys Cys Ala Gly Cys Ala Gly Ala Ala Cys Ala Cys
545 550 555 560

Cys Cys Cys Cys Ala Thr Cys Gly Gly Cys Gly Ala Cys Gly Gly Cys
565 570 575

Cys Cys Cys Gly Thr Gly Cys Thr Gly Cys Thr Gly Cys Cys Cys Gly
580 585 590

Ala Cys Ala Ala Cys Cys Ala Cys Thr Ala Cys Cys Thr Gly Ala Gly
595 600 605

Cys Ala Cys Cys Cys Ala Gly Thr Cys Cys Gly Cys Cys Cys Thr Gly
610 615 620

Ala Gly Cys Ala Ala Ala Gly Ala Cys Cys Cys Cys Ala Ala Cys Gly
625 630 635 640

Ala Gly Ala Ala Gly Cys Gly Cys Gly Ala Thr Cys Ala Cys Ala Thr
645 650 655

Gly Gly Thr Cys Cys Thr Gly Cys Thr Gly Gly Ala Gly Thr Thr Cys
660 665 670

Gly Thr Gly Ala Cys Cys Gly Cys Cys Gly Cys Cys Gly Gly Gly Ala
675 680 685

Thr Cys Ala Cys Thr Cys Thr Cys Gly Gly Cys Ala Thr Gly Gly Ala
690 695 700

Cys Gly Ala Gly Cys Thr Gly Thr Ala Cys Ala Ala Gly Thr Ala Ala
705 710 715 720

Ala Gly Cys Gly

<210> SEQ ID NO 13
<211> LENGTH: 724
<212> TYPE: PRT
<213> ORGANISM: Artificial Sequence
<220> FEATURE:
<223> OTHER INFORMATION: Synthetic Polynucleotide

<400> SEQUENCE: 13

Gly Cys Gly Ala Ala Ala Thr Gly Ala Ala Cys Ala Thr Gly Thr Cys
1 5 10 15

Gly Ala Gly Cys Ala Gly Gly Thr Ala Cys Gly Gly Cys Thr Cys Thr
20 25 30

Cys Ala Cys Thr Ala Gly Gly Gly Cys Cys Gly Cys Cys Gly Cys Cys
35 40 45

Ala Gly Thr Gly Cys Thr Thr Gly Ala Gly Gly Thr Cys Gly Thr Cys
50 55 60

Cys Thr Gly Gly Thr Ala Cys Ala Cys Thr Ala Gly Cys Gly Cys Gly
65 70 75 80

Ala Ala Gly Ala Gly Cys Ala Ala Cys Cys Cys Cys Ala Gly Ala Ala
85 90 95

Ala Cys Gly Ala Gly Thr Cys Cys Cys Gly Cys Cys Thr Gly Ala Cys
100 105 110

Cys Cys Ala Cys Gly Ala Gly Thr Cys Cys Ala Thr Cys Ala Cys Cys
115 120 125

Ala Ala Cys Ala Gly Cys Cys Cys Gly Thr Cys Gly Thr Cys Gly Thr
130 135 140

Gly Cys Cys Cys Cys Gly Gly Cys Ala Gly Cys Gly Gly Cys Thr Ala
145 150 155 160

Cys Cys Cys Cys Cys Ala Cys Ala Ala Gly Ala Cys Gly Ala Cys Cys
165 170 175

Ala Thr Cys Ala Cys Cys Ala Gly Cys Cys Gly Cys Thr Cys Gly Ala
180 185 190

Cys Gly Thr Gly Cys Gly Ala Cys Gly Gly Cys Ala Gly Gly Ala Gly
195 200 205

Cys Thr Ala Cys Ala Ala Cys Ala Cys Cys Gly Cys Cys Thr Ala Gly
210 215 220

Ala Ala Cys Thr Thr Cys Ala Ala Gly Thr Gly Gly Ala Ala Cys Thr
225 230 235 240

Ala Cys Gly Gly Cys Ala Ala Gly Ala Ala Gly Ala Cys Gly Ala Ala
245 250 255

Cys Ala Gly Cys Cys Gly Gly Thr Ala Cys Thr Ala Thr Ala Thr Cys
260 265 270

Thr Gly Cys Ala Ala Cys Ala Cys Cys Gly Ala Cys Ala Ala Cys Ala
275 280 285

Thr Cys Ala Ala Cys Ala Thr Gly Ala Gly Gly Thr Cys Gly Ala Ala
290 295 300

Cys Ala Cys Gly Gly Gly Gly Thr Cys Cys Thr Ala Cys Ala Ala Cys
305 310 315 320

Gly Gly Cys Ala Gly Gly Ala Gly Gly Ala Ala Cys Thr Thr Cys Ala
325 330 335

Gly Cys Thr Ala Cys Gly Gly Gly Ala Ala Gly Thr Cys Gly Ala Gly
340 345 350

Cys Thr Ala Cys Gly Cys Cys Ala Ala Gly Thr Gly Gly Thr Cys Cys
355 360 365

Cys Ala Cys Ala Gly Cys Gly Gly Ala Gly Cys Thr Thr Gly Ala
370                 375                 380

Ala Gly Thr Gly Gly Ala Gly Cys Cys Gly Cys Gly Cys Cys Ala
385                 390                 395                 400

Gly Ala Ala Cys Ala Thr Cys Ala Ala Cys Gly Gly Cys Ala Gly Cys
            405                 410                 415

Ala Gly Gly Ala Ala Cys Thr Thr Cys Thr Thr Cys Thr Ala Cys Cys
420                 425                 430

Ala Cys Gly Cys Gly Ala Gly Gly Ala Cys Cys Thr Gly Cys Ala Thr
        435                 440                 445

Cys Gly Gly Ala Ala Gly Cys Cys Cys Gly Thr Ala Cys Cys Gly Cys
450                 455                 460

Cys Thr Gly Ala Ala Cys Thr Thr Cys Thr Thr Cys Ala Gly Cys Ala
465                 470                 475                 480

Cys Gly Ala Cys Gly Ala Ala Gly Thr Ala Cys Ala Cys Cys Ala Gly
        485                 490                 495

Cys Cys Cys Cys Ala Thr Cys Gly Cys Cys Gly Ala Cys Thr Thr Cys
            500                 505                 510

Gly Thr Gly Ala Cys Gly Thr Gly Cys Gly Gly Cys Ala Thr Cys Cys
515                 520                 525

Ala Gly Thr Cys Cys Cys Ala Cys Cys Ala Gly Thr Gly Cys Thr Cys
530                 535                 540

Cys Cys Ala Cys Cys Cys Gly Gly Thr Cys Cys Gly Thr Gly Cys
545                 550                 555                 560

Cys Cys Gly Thr Cys Gly Ala Ala Cys Gly Gly Cys Cys Ala Cys Cys
        565                 570                 575

Ala Cys Gly Thr Cys Thr Ala Cys Thr Thr Gly Ala Ala Gly Thr Cys
            580                 585                 590

Cys Cys Ala Gly Thr Cys Gly Ala Ala Cys Gly Gly Cys Ala Thr Cys
595                 600                 605

Cys Ala Cys Cys Gly Thr Ala Gly Cys Gly Gly Gly Ala Gly Cys Gly
610                 615                 620

Gly Gly Ala Gly Cys Gly Gly Cys Cys Thr Gly Thr Gly Cys Gly Ala
625                 630                 635                 640

Cys Thr Thr Gly Ala Ala Cys Ala Cys Cys Gly Gly Cys Ala Ala Ala
            645                 650                 655

Thr Gly Cys Ala Gly Cys Gly Gly Cys Ala Gly Gly Thr Cys Gly Ala
            660                 665                 670

Gly Cys Thr Gly Gly Thr Cys Cys Thr Ala Cys Cys Cys Gly Thr Gly
        675                 680                 685

Gly Thr Gly Gly Gly Cys Cys Ala Cys Thr Thr Gly Thr Cys Gly Gly
690                 695                 700

Ala Gly Gly Ala Gly Cys Gly Gly Gly Ala Ala Cys Gly Ala Gly Thr
705                 710                 715                 720

Gly Gly Thr Ala

<210> SEQ ID NO 14
<211> LENGTH: 1686
<212> TYPE: DNA
<213> ORGANISM: Artificial Sequence
<220> FEATURE:
<223> OTHER INFORMATION: Synthetic Polynucleotide

<400> SEQUENCE: 14

```
tttggtggag cgcttgtttc gttttataca aacttttaa atactatttg gccaagtgaa      60
gacccgtgga aggcttttat ggaacaagta gaagcattga tggatcagaa aatagctgat     120
tatgcaaaaa ataaagctct tgcagagtta cagggccttc aaaataatgt cgaagattat    180
gtgagtgcat tgagttcatg gcaaaaaaat cctgtgagtt cacgaaatcc acatagccag    240
gggcggataa gagagctgtt ttctcaagca gaaagtcatt ttcgtaattc aatgccttcg    300
tttgcaattt ctggatacga ggttctattt ctaacaacat atgcacaagc tgccaacata    360
catttatttt tactaaaaga cgctcaaatt tatggagaag aatggggata cgaaaaagaa    420
gatattgctg aatttataa aagacaacta aacttacgc aagaatatac tgaccattgt      480
gtcaaatggt ataatgttgg attagataaa ttaagaggtt catcttatga atcttgggta    540
aactttaacc gttatcgcag agagatgaca ttaacagtat tagatttaat tgcactattt    600
ccattgtatg atgttcggct atacccaaaa gaagttaaaa ccgaattaac aagagacgtt    660
ttaacagatc caattgtcgg agtcaacaac cttaggggct atggaacaac cttctctaat    720
atagaaaatt atattcgaaa accacatcta tttgactatc tgcatagaat tcaatttcac    780
acgcggttcc gaccaggata ctatggaaat gactctttca attattggtc cggtaattat    840
gtttcaacta gaccaagcat aggatcaaat gatataatca catctccatt ctatggaaat    900
aaatccagtg aacctgtaca aaatttagaa tttaatggag aaaaagtcta tagagccgta    960
gcaaatacaa atcttgcggt ctggccgtcc gctgtatatt caggtgttac aaaagtggaa   1020
tttagccaat ataatgatca aacagatgaa gcaagtacac aaacgtacga ctcaaaaaga   1080
aatgttggcg cggtcagctg ggattctatc gatcaattgc ctccagaaac aacagatgaa   1140
cctccagaaa agggatatag ccatcaactc aattatgtaa tgtgcttttt aatgcagggt   1200
agtgaggaa caatcccagt gttaacttgg acacataaaa gtgtagactt ttttaacatg    1260
attgattcga aaaaattac acaacttccg ttagtaaagg catataagtt acaatctggt    1320
gcttccgttg tcgcaggtcc taggtttaca ggaggagata tcattcaatg cacagaaaat   1380
ggaagtgcgg caactattta cgttacaccg gatgtgtcgt actctcaaaa acatcgagct   1440
agaattcatt atgcttctac atctcagata acatttacac tcagtttaga cggggcacca   1500
tttaatcaat actatttcga taaaacgata aataaaggag acacattaac gtataattca   1560
tttaatttag caagtttcag cacaccattc gaattatcgg ggaataactt acaaatagg    1620
gtcacaggat taagtgctgg agataaagtt tatatagaca aaattgaatt tattccagtg   1680
aattaa                                                               1686
```

<210> SEQ ID NO 15
<211> LENGTH: 1686
<212> TYPE: DNA
<213> ORGANISM: Artificial Sequence
<220> FEATURE:
<223> OTHER INFORMATION: Synthetic Polynucleotide

<400> SEQUENCE: 15

```
aattaagtga cctttatttaa gttaaaacag atatatttga aatagaggtc gtgaattagg    60
acactgcgga taaacattca ataagggct attaagctta ccacacgact ttgaacgatt    120
taatttactt aatatgcaat tacacagagg aaataaaatag caaaatagct ttatcataac   180
taatttacca cggggcagat ttgactcaca tttacaatag actctacatc ttcgtattac   240
ttaagatcga gctacaaaaa ctctcatgct gtgtaggcca cattgcattt atcaacggcg   300
tgaaggtaaa agacacgtaa cttactatag aggaggacat ttggatcctg gacgctgttg   360
```

-continued

```
ccttcgtggt ctaacattga atatacggaa atgattgcct tcaacacatt aaaaaaagct      420
tagttagtac aatttttcca gatgtgaaaa tacacaggtt caattgtgac cctaacaagg      480
agatgatggg acgtaatttt tcgtgtaatg tattaactca actaccgata tagggaaaag      540
acctccaagt agacaacaaa gacctccgtt aactagctat cttagggtcg actggcgcgg      600
ttgtaaagaa aaactcagca tgcaaacaca tgaacgaagt agacaaacta gtaatataac      660
cgatttaagg tgaaaacatt gtggacttat atgtcgcctg ccggtctggc gttctaaaca      720
taaacgatgc cgagatatct gaaaagagg taatttaaga tttaaaacat gtccaagtga       780
cctaaataaa ggtatcttac ctctacacta atatagtaaa ctaggatacg aaccagatca      840
actttgtatt aatggcctgg ttattaactt tctcagtaaa ggtatcatag gaccagcctt      900
ggcgcacact ttaacttaag atacgtctat cagtttatct acaccaaaag cttatattaa      960
aagatataat ctcttccaac aaggtatcgg ggattccaac aactgaggct gttaacctag     1020
acaattttgc agagaacaat taagccaaaa ttgaagaaaa cccatatcgg cttgtagtat     1080 gttacccttta tcacgttaat ttagattatg acaattacag tagagagacg ctattgccaa    1140
tttcaaatgg gttctaagta ttctacttgg agaattaaat agattaggtt gtaatatggt     1200
aaactgtgtt accagtcata taagaacgca ttcaaaatca acagaaaata ttttaagtcg     1260
ttatagaaga aaaagcatag gggtaagaag aggtatttaa actcgcagaa aatcattttt     1320
atttacatac aaccgtcgaa cacgtataca acaatcttta tcttggagca taggtcttta     1380
acgtttgctt ccgtaactta atgcttttac tgaaagacga actctttgt cgagagaata      1440 ggcggggacc gatacaccta agcacttga gtgtcctaaa aaaacggtac ttgagttacg      1500
tgagtgtatt agaagctgta ataaaacttc cgggacattg agacgttctc gaaataaaaa     1560
acgtattagt cgataaaaga ctaggtagtt acgaagatga acaaggtatt tcggaaggt      1620 gcccagaagt gaaccggttt atcataaatt tttcaaacat attttgcttt gttcgcgagg     1680
tggttt                                                                1686
```

<210> SEQ ID NO 16
<211> LENGTH: 696
<212> TYPE: DNA
<213> ORGANISM: Artificial Sequence
<220> FEATURE:
<223> OTHER INFORMATION: Synthetic Polynucleotide

<400> SEQUENCE: 16

```
atgttcttca accgcgttat caccttgacc gttccaagca gcgatgtcgt taactacagc       60
gaaatctacc aggtcgctcc acagtatgtt aaccaggctt tgaccttggc taagtacttc      120
cagggagcta tcgatggtag caccttgaga ttcgatttcg agaaggcttt gcagattgct      180
aacgatattc cacaggcagc cgtggtcaac accttgaatc agactgtcca gcaaggtact      240
gtccaagtca gcgtgatgat cgacaagatt gtcgacatta tgaagaatgt gttgagcatt      300
gtcattgata acaaaaagtt ctgggatcag gtgactgctg ctattactaa taccttcacc      360
aacttgaaca gccaagaaag cgaaagatgg attttctact acaaggaaga tgctcacaag      420
actagctact attacaatat cttgtttgct attcaggatg aggaaactgg tggcgttatg      480
gccaccttgc caatcgcctt tgatattagc gttgatattg aaaaggaaaa ggttttgttt     540
gttactatca aggatactga gaattacgct gttaccgtga agctatcaa cgtcgttcag      600 gctttgcaaa gcagcagaga tagcaaagtt gtggatgctt taaaagccc aagacacttg      660
```

```
ccaagaaaaa gacacaaaat ctgcagcaac agctaa                              696
```

```
<210> SEQ ID NO 17
<211> LENGTH: 696
<212> TYPE: DNA
<213> ORGANISM: Artificial Sequence
<220> FEATURE:
<223> OTHER INFORMATION: Synthetic Polynucleotide

<400> SEQUENCE: 17
aatcgacaac gacgtctaaa acacagaaaa agaaccgttc acagaacccg aaaattttcg     60
taggtgttga acgatagag acgacgaaac gtttcggact tgctgcaact atcgaaagtg    120
ccattgtcgc attaagagtc ataggaacta tcattgtttg ttttggaaaa ggaaaagtta    180
tagttgcgat tatagtttcc gctaaccgtt ccaccggtat tgcggtggtc aaaggagtag    240
gacttatcgt ttgttctata acattatcat cgatcagaac actcgtagaa ggaacatcat    300
cttttaggta gaaagcgaaa gaaccgacaa gttcaaccac ttccataatc attatcgtcg    360
tcagtggact agggtcttga aaaacaatag ttactgttac gagttgtgta agaagtatta    420
cagctgttag aacagctagt agtgcgactg aacctgtcat ggaacgacct gtcagactaa    480
gttccacaac tggtgccgac ggacaccta tagcaatcgt tagacgtttc ggaagagctt    540
tagcttagag ttccacgatg gtagctatcg agggaccttc atgaatcggt tccagtttcg    600
gaccaattgt atgacacctc gctggaccat ctaaagcgac atcaattgct gtagcgacga    660
accttgccag ttccactatt gcgccaactt cttgta                              696
```

```
<210> SEQ ID NO 18
<211> LENGTH: 474
<212> TYPE: DNA
<213> ORGANISM: Artificial Sequence
<220> FEATURE:
<223> OTHER INFORMATION: Synthetic Polynucleotide

<400> SEQUENCE: 18
atggctaagg caagtctcct cattttggct accatctttc ttggagtcat cacaccagct     60
tgcctgagtg aaaatattct gtactccggt gagactctcc ctacagggg atttctcacc    120 tctggcagtt ttgtttttat catgcaagag gactgcaacc tggtcttgta caacgtcgac    180
aagcccatct gggcaactaa cacaggcggc ctctccagtg actgctccct cagcatgcag    240
accgatggga acctcgttgt gtacaccca tcggacaaac cgatttgggc aagcgacact    300
gacggtcaga atgggaatta cgtgtgcatc catcaaaagg atcggaacgt tgtgatctac    360
ggaactaatc gttgggctac tggaactcac accggcgctg taggaattcc tgcatcaccg    420
ccctcggaga aatatcctac tgctggaatg ataaagcttg tgacggcaaa gtaa          474
```

```
<210> SEQ ID NO 19
<211> LENGTH: 474
<212> TYPE: DNA
<213> ORGANISM: Artificial Sequence
<220> FEATURE:
<223> OTHER INFORMATION: Synthetic Polynucleotide

<400> SEQUENCE: 19
aatgaaacgg cagtgttcga aatagtaagg tcgtcatcct ataaagaggc tcccgccact     60
acgtccttaa ggatgtcgcg gccacactca aggtcatcgg gttgctaatc aaggcatcta    120
gtgttgcaag gctaggaaaa ctacctacgt gtgcattaag ggtaagactg gcagtcacag    180
cgaacgggtt tagccaaaca ggctaccca catgtgttgc tccaagggta gccagacgta    240
```

```
cgactccctc gtcagtgacc tctccggcgg acacaatcaa cgggtctacc cgaacagctg    300
caacatgttc tggtccaacg tcaggagaac gtactatttt tgttttgacg gtctccactc    360
tttaggggga catccctctc agagtggcct catgtcttat aaaagtgagt ccgttcgacc    420
acactactga ggttctttct accatcggtt ttactcctct gaacggaatc ggta          474
```

<210> SEQ ID NO 20
<211> LENGTH: 500
<212> TYPE: DNA
<213> ORGANISM: Artificial Sequence
<220> FEATURE:
<223> OTHER INFORMATION: Synthetic Polynucleotide

<400> SEQUENCE: 20

```
actcctttac tattttcctt tgcgtttaca tcgcttgcta ttacacctat cgctgtttgt     60
gtaccatctg tggcagttgg atttaaagct taattaaat tatctttagt atcataacca     120
actactgttc ctagcttcag attttgtccc tttgctaccg ttatttggtc tcttgaatat    180
aaacttgatg cctcatactt taataggtca cctagattat tttgttcggt tatacatgtc    240
atattttctt ttctccttt ttcctttagt tttaccgcca tgtttgtagt tattgtatgc     300
ggcggttata aaaaaactta aatacttgat tgtgctctag cttttgctac ttgcatcatc    360
aaatcttctc ctgaattctg tggtattgca ctcagtatct ctgtcttctt cgttctctct    420
gcaagtaatt ccattaaaac ttcccttgct tgctcaatac ttacaccctg ctcaataaat    480 tctcctatt tctctgacat                                                 500
```

<210> SEQ ID NO 21
<211> LENGTH: 561
<212> TYPE: DNA
<213> ORGANISM: Artificial Sequence
<220> FEATURE:
<223> OTHER INFORMATION: Synthetic Polynucleotide

<400> SEQUENCE: 21

```
tcgtgataag ttacataaac gtattaattc aacaacttca gtacgatact tagttaaatt     60
atcagtttct aggtcacttg tagtttgttt attcatagta ttttctcctt tgttaataaa    120
ttcaaaaaat gttgtaactc catctgcaag acctatttct actgctttct caccaaaata    180
tagacctgct tcagtatttt ttattgcttg tacagaaagt cctctgtttc gtgctataag    240
ttcagtcaga atttcatata agcgatttac ttcctcctct aaacttttta agctttctaa    300
acttataggc tcatgtggat ttaaatcatt ctttctcttg cctgcaaaaa tagttgtgta    360
ttttattcct tgcttttcat caaacctact tgatctata tgacttgcta ttactcctat    420
actgccaaca ccaaaagttc tgctcacaaa taccttttca gcacttgaag ctatagcata    480
tgcagcagag tacgcatcat catttgctat tgccacaatt ctctttttg ctcttgattc    540 gtaaataaaa tcagccaagt c                                              561
```

<210> SEQ ID NO 22
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 22

```
agggctttac tcaaaattgg                                                 20
```

```
<210> SEQ ID NO 23
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 23
caccaacggt atggagtgat agg                                            23

<210> SEQ ID NO 24
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 24
ggtgaacttc aagatccgcc                                                20

<210> SEQ ID NO 25
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 25
cttgtacagc tcgtccatgc                                                20

<210> SEQ ID NO 26
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 26
caggtacggc tctcactagg                                                20

<210> SEQ ID NO 27
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 27
taccggctgt tcgtcttctt                                                20

<210> SEQ ID NO 28
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 28
ttgtcgcagg tcctaggttt                                                20

<210> SEQ ID NO 29
<211> LENGTH: 20
<212> TYPE: DNA
<213> ORGANISM: Artificial Sequence
<220> FEATURE:
<223> OTHER INFORMATION: Synthetic Polynucleotide
```

<400> SEQUENCE: 29
aatggtgccc cgtctaaact                                          20

<210> SEQ ID NO 30
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 30
gtgtaggcca cattgcattt atc                                      23

<210> SEQ ID NO 31
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 31
cgtcccatca tctccttgtt ag                                       22

<210> SEQ ID NO 32
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 32
gatcaggtga ctgctgctat ta                                       22

<210> SEQ ID NO 33
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 33
ctttgctatc tctgctgctt tg                                       22

<210> SEQ ID NO 34
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 34
gaaagcgaaa gaaccgacaa g                                        21

<210> SEQ ID NO 35
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 35
gctaccatcg tggaactcta ag                                       22

<210> SEQ ID NO 36

-continued

<210> SEQ ID NO 36
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 36
ggctaccatc tttcttggag tc                                            22

<210> SEQ ID NO 37
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 37
ctttgccgtc acaagcttta tc                                            22

<210> SEQ ID NO 38
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 38
acactcaagg tcatcgggtt                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 39
ccagaacatg ttgcagctgt                                               20

<210> SEQ ID NO 40
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 40
ataaattctc ctattttctc tggcattcgt gataagttac ata                     43

<210> SEQ ID NO 41
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 41
ataaattctc ctattttctc tgacattcgt gataagttac ata                     43